US010946200B2

(12) United States Patent
Aghassian

(10) Patent No.: US 10,946,200 B2
(45) Date of Patent: *Mar. 16, 2021

(54) PLUG-IN ACCESSORY FOR CONFIGURING A MOBILE DEVICE INTO AN EXTERNAL CONTROLLER FOR AN IMPLANTABLE MEDICAL DEVICE

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 10 days.

This patent is subject to a terminal disclaimer.

(21) Appl. No.: 16/282,128

(22) Filed: Feb. 21, 2019

(65) Prior Publication Data

US 2019/0184182 A1 Jun. 20, 2019

Related U.S. Application Data

(63) Continuation of application No. 15/649,470, filed on Jul. 13, 2017, now Pat. No. 10,252,064, which is a continuation of application No. 14/599,743, filed on Jan. 19, 2015, now Pat. No. 9,707,402.

(60) Provisional application No. 61/986,809, filed on Apr. 30, 2014, provisional application No. 61/940,273, filed on Feb. 14, 2014.

(51) Int. Cl.
*A61N 1/372* (2006.01)
*H04M 1/725* (2021.01)

(52) U.S. Cl.
CPC ...... *A61N 1/37229* (2013.01); *A61N 1/37247* (2013.01); *H04M 1/7253* (2013.01); *H04M 1/72527* (2013.01)

(58) Field of Classification Search
CPC .............................. A61N 1/3787; A61N 1/08
See application file for complete search history.

(56) References Cited

U.S. PATENT DOCUMENTS

| 7,177,698 | B2 | 2/2007 | Klosterman et al. |
| 7,962,222 | B2 | 6/2011 | He et al. |
| 8,126,731 | B2 | 2/2012 | Dicks et al. |
| 8,214,042 | B2 | 7/2012 | Ozawa et al. |

(Continued)

OTHER PUBLICATIONS

U.S. Appl. No. 61/789,700, dated Jun. 3, 2013, Kothandaraman.

(Continued)

*Primary Examiner* — Joseph M Dietrich
(74) *Attorney, Agent, or Firm* — Lewis & Reese, PLLC

(57) ABSTRACT

Disclosed is a plug-in accessory for operating a mobile device as an external controller for an Implantable Medical Device (IMD). The accessory includes a connector insertable into a port on the mobile device. Accessory circuitry can be powered by a battery or by the mobile device. An application on the mobile device in conjunction with the accessory configures the mobile phone for immediate use as an IMD external controller. When the accessory is inserted into the port or a switch on the accessory pressed, the application operates to validate the accessory; to unlock the phone; to secure the mobile device; and to render a graphical user interface on the mobile device for communicating with the IMD. The accessory can additionally include telemetry circuitry and an antenna for communicating with the IMD, rather than using short-range communication means provided in the mobile device itself.

20 Claims, 15 Drawing Sheets

(56) References Cited

U.S. PATENT DOCUMENTS

| | | |
|---|---|---|
| 8,335,569 B2 | 12/2012 | Aghassian |
| 8,463,392 B2 | 6/2013 | Aghassian |
| 8,498,716 B2 | 7/2013 | Chen et al. |
| 8,543,208 B2 | 9/2013 | Pless et al. |
| 8,588,925 B2 | 11/2013 | Carbunaru et al. |
| 8,682,444 B2 | 3/2014 | Aghassian et al. |
| 2008/0103370 A1 | 5/2008 | Dicks |
| 2014/0354211 A1 | 12/2014 | Zottola et al. |
| 2015/0066110 A1 | 3/2015 | Tahmasian |
| 2015/0073498 A1 | 3/2015 | Kothandaraman |
| 2015/0073500 A1 | 3/2015 | Kothandaraman et al. |

OTHER PUBLICATIONS

Energy Micro, EFM®32, Connect the EFM32 with a Smart Phone through the Audio Jack, Rev.1.03 (May 2013).
Supersonic IQ-209 FM transmitter, Spec Sheet (date unknown).
Naztech N3030 Universal FM Transmitter, Spec Sheet (date unknown).

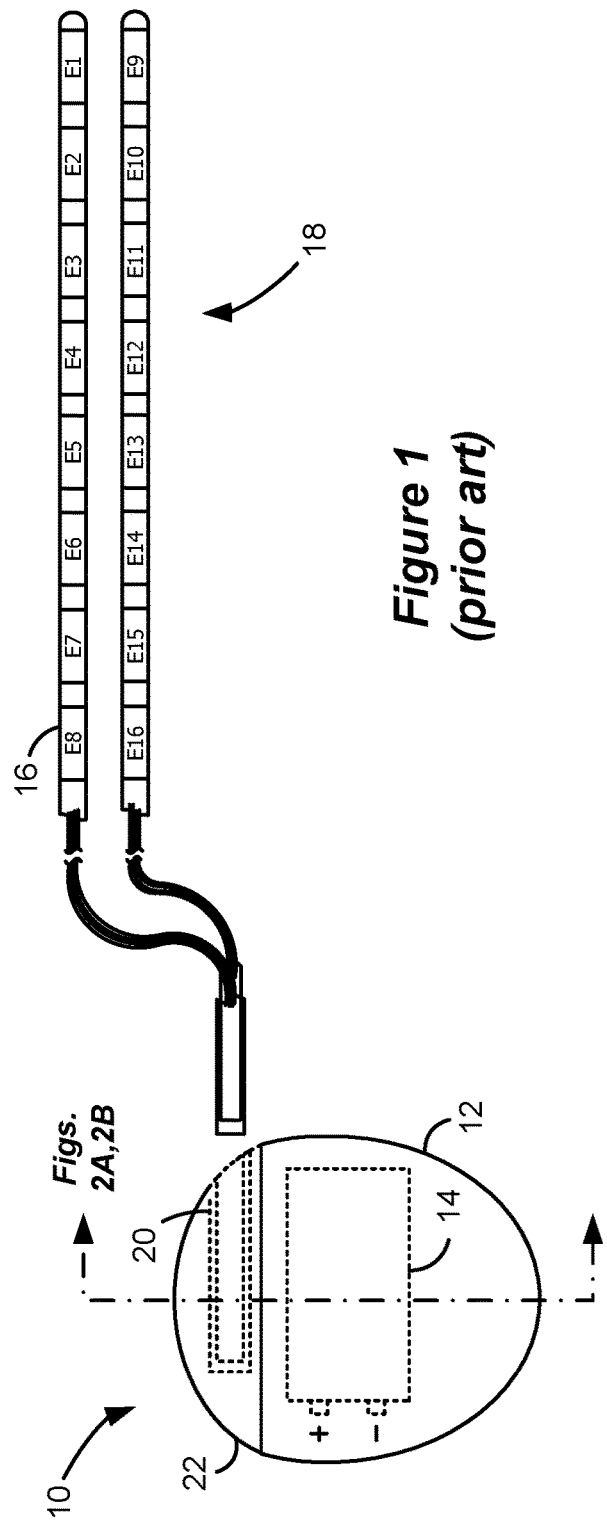
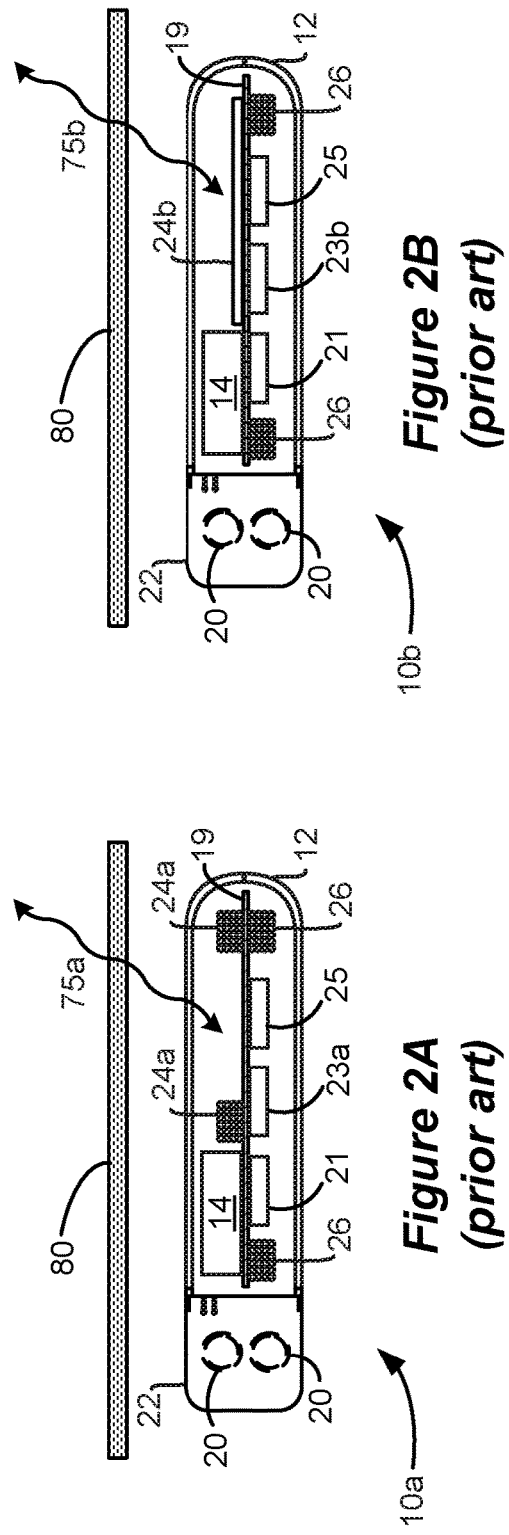
Figure 1 (prior art)
Figure 2A (prior art)
Figure 2B (prior art)

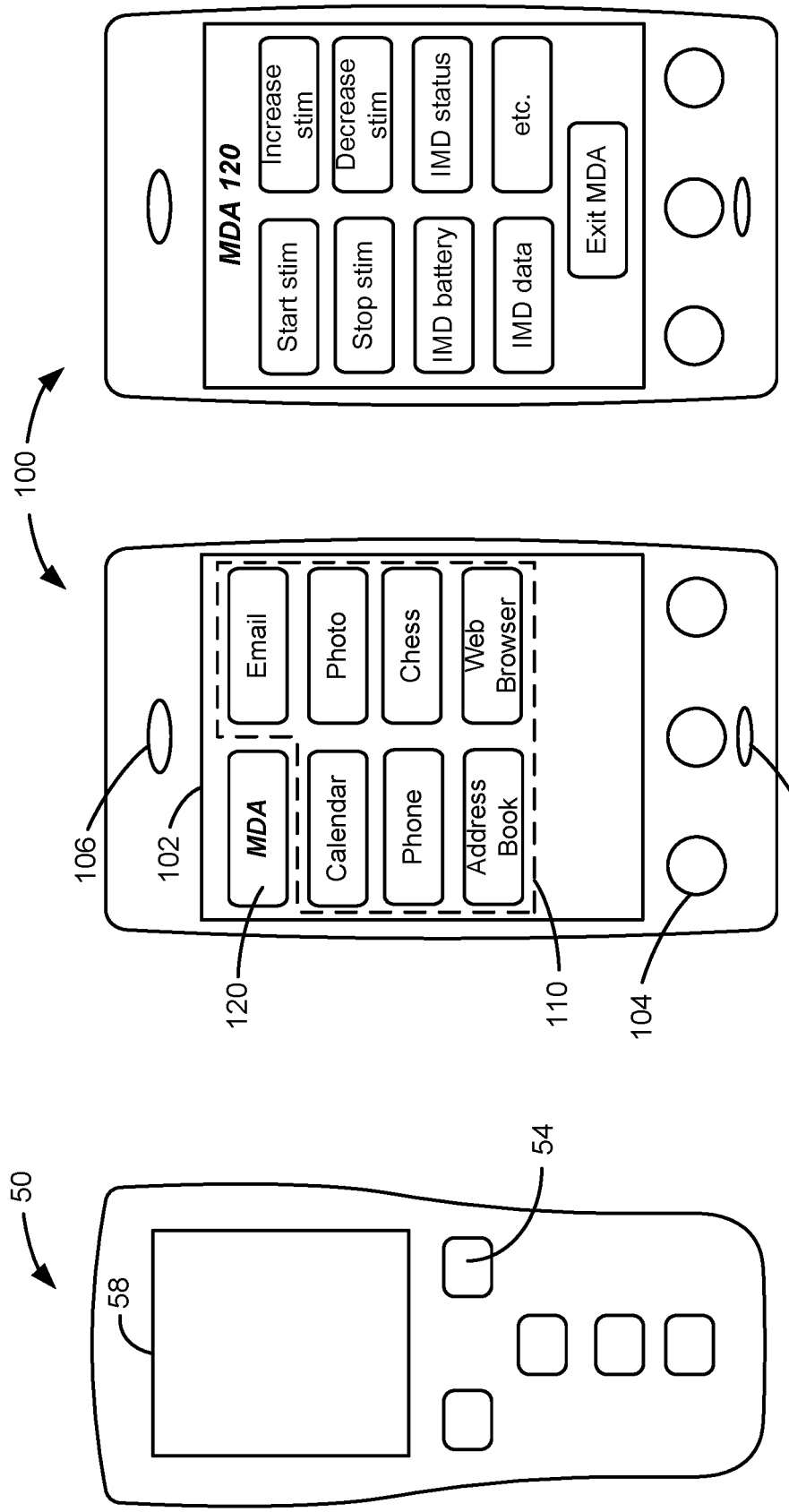

PLUG-IN ACCESSORY FOR CONFIGURING A MOBILE DEVICE INTO AN EXTERNAL CONTROLLER FOR AN IMPLANTABLE MEDICAL DEVICE

CROSS-REFERENCE TO RELATED APPLICATIONS

This application is a continuation of U.S. application Ser. No. 15/649,470, filed Jul. 13, 2017 (allowed), which is a continuation of U.S. application Ser. No. 14/599,743, filed Jan. 19, 2015 (now U.S. Pat. No. 9,707,402), which is a non-provisional application of U.S. Provisional Patent Application Ser. Nos. 61/986,809, filed Apr. 30, 2014, and 61/940,273, filed Feb. 14, 2014. Priority is claimed to these applications, and they are incorporated herein by reference in their entireties.

FIELD OF THE INVENTION

The present invention relates generally to implantable medical device systems, and more particularly, to an accessory useable with a mobile external device to facilitate wireless communications with an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device (IMD) or in any implantable medical device system.

As shown in FIG. 1, a SCS system includes an implantable pulse generator 10 (hereinafter, and more generically, IMD 10), which includes a biocompatible device case 12 formed of titanium for example. The case 12 typically holds the circuitry and battery 14 necessary for the IMD 10 to function. The IMD 10 is coupled to electrodes 16 via one or more electrode leads 18 (two of which are shown). The proximal ends of the leads 18 are coupled to the IMD 10 at one or more lead connectors 20 fixed in a header 22, which can comprise an epoxy for example. In the illustrated embodiment, there are sixteen electrodes, although the number of leads and electrodes is application specific and therefore can vary. In an SCS application, two electrode leads 18 are typically implanted on the right and left side of the dura within the patient's spinal column. The proximal ends of the leads 18 are then tunneled through the patient's flesh to a distant location, such as the buttocks, where the IMD case 12 is implanted, at which point they are coupled to the lead connectors 20.

Cross sections of two examples of IMD 10, 10a and 10b, are shown in FIGS. 2A and 2B. Both contain a charging coil 26 for wirelessly charging the IMD's battery 14 using an external charging device (not shown). (If battery 14 is not rechargeable, charging coil 26 can be dispensed with). Both IMDs 10a and 10b also contain control circuitry such as a microcontroller 21, telemetry circuitry 23 (discussed further below), and various components 25 necessary for IMD operation, such as stimulation circuitry for forming therapeutic pulses at the electrodes 16. The charging coil 26, battery 14, microcontroller 21, telemetry circuitry 23, and other components 25 are electrically coupled to a printed circuit board (PCB) 19.

Different in the two IMDs 10a and 10b are the telemetry antennas 24a and 24b used to transcutaneously communicate data through the patient's tissue 80 with devices external to the patient (not shown in FIGS. 2A and 2B). In IMD 10a (FIG. 2A), the antenna comprises a coil 24a, which can bi-directionally communicate with an external device along a magnetic induction communication link 75a. Telemetry circuitry 23a is electrically coupled to the antenna coil 24a to enable it to communicate via magnetic induction link 75a, which comprises a magnetic field of typically less than 10 MHz operable in its near-field to communicate at a distance of 12 inches or less for example. Telemetry circuitry 23a generally includes driver circuitry for energizing the antenna coil 24a to transmit data and amplifier/filter circuitry for resolving data received at the coil 24a. Telemetry circuitry 23a generally also operates in accordance with a modulation scheme (defining how data to be transmitted is modulated on the link 75a and will be demodulated when received) and a communication protocol (defining the manner in which the data is formatted). Telemetry circuitry 23a receives the data to be transmitted in digital form from the microcontroller 21, and provides received digital data to the microcontroller 21 for interpretation. A typical modulation scheme used by telemetry circuitry 23a is Frequency Shift Keying (FSK), although other modulation schemes could also be used. In FIG. 2A, the external device would also contain communication means (e.g., a coil antenna; telemetry circuitry) compatible with the magnetic induction link 75a and the protocol used by the IMD 10a.

In IMD 10b (FIG. 2B), short-range Radio Frequency (RF) communication means—including short-range RF antenna 24b and compliant short-range RF telemetry circuitry 23b—are provided that operate in accordance with a short-range RF communication standard and its underlying protocols to bi-directionally communicate with an external device along a short-range RF communication link 75b. RF communication link 75b typically operates using far-field electromagnetic waves ranging from 10 MHz to 10 GHz or so. Short-range RF standards supported by short-range RF telemetry circuitry 23b and antenna 24b include, for example, Bluetooth, BLE, NFC, Zigbee, WiFi, and the Medical Implant Communication Service (MICS). Short-range RF antenna 24b can take any number of well-known forms for an electromagnetic antenna, such as patches, slots, wires, etc., and can operate as a dipole or a monopole. The external device in FIG. 2B would also contain short-range RF communication means compatible with RF link 75b and the standard/protocol used in IMD 10b. As used herein, "short-range" RF telemetry may allow communications between devices (e.g., an external device and IMD 10b) at distances of about 50 feet or less.

Although both of antennas 24a and 24b in IMDs 10a and 10b are shown in FIGS. 2A and 2B inside of case 12, they may also be placed within the IMD's header 22, or on the outside of the case 12.

Different configurations for external devices used to communicate with IMDs such as 10a and 10b exist in the prior art. Such external devices are typically used to send or adjust the therapy settings the IMD 10*a* or 10*b* will provide to the patient (such as which electrodes 16 are active to issue pulses; whether such electrodes sink or source current (i.e., polarity); the duration, frequency, and amplitude of pulses, etc.), which settings together comprise a stimulation program for the patient. External devices can also act as receivers of data from the IMD 10*a* or 10*b*, such as various data reporting on the IMD's status and the level of the IMD's battery 14.

An external device having such functionality is shown in FIG. 3 in the form of a patient remote control (external controller) 50. External controller 50 is typically hand-held, portable, and powered by a battery. The external controller 50 includes a user interface similar to that used for a cell phone, including buttons 54 and a display 58, and may have other interface aspects as well, such as a speaker. Although not shown, the external controller 50 would also include within its housing communication means (including a coil antenna or a short-range RF antenna) compatible with the link 75*a* or 75*b* and the communication means in the IMD 10*a* or 10*b*.

External devices such as the external controller 50 of FIG. 3 were historically built by the manufacturer of the IMDs, and thus were generally dedicated to communicate only with such IMDs. However, there are many commercial mobile devices, such as cell phones, that have user interfaces and built-in communication means suitable for functioning as a wireless external controller for an IMD. Using such mobile devices as external controllers for IMDs would benefit both manufacturers and patients: manufacturers would not need to design, build, and test dedicated external controllers, and patients could control and communicate with their IMDs without the inconvenience of having to carry and purchase additional custom external controllers.

FIGS. 4A and 4B show an example of a mobile device 100 configured for use as an external controller for an IMD, as described in commonly-owned U.S. Pat. No. 9,186,518, which is incorporated herein by reference. The mobile device 100 may be a commercial, multipurpose, consumer device, such as a cell phone, tablet, personal data assistant, laptop or notebook computer, or like device—essentially any mobile, hand-holdable device capable of functioning as a wireless external controller for an IMD. Examples include the Apple iPhone or iPad, Microsoft Surface, Nokia Lumia devices, Samsung Galaxy devices, and Google Android devices for example.

As shown in FIG. 4A, the mobile device 100 includes a user interface with a display 102, which may also receive input if it is a touch screen. The mobile device 100 may also have buttons 104 (e.g., a keyboard) for receiving input from the patient, a speaker 106, and a microphone 108. Shown on the display 102 is a typical home screen graphical user interface provided by the mobile device 100 when first booted or reset. A number of applications ("apps") 110 may be present and displayed as icons on the mobile device home screen, which the patient can select and execute.

One of the applications (icons) displayed in FIG. 4A is a Medical Device Application (MDA) 120, which when executed by the patient will configure the mobile device 100 for use as an external controller to communicate with an IMD. FIG. 4B shows the home screen of the MDA 120 after it is executed, which includes options selectable by a patient to control his stimulation program or monitor his IMD. For example, the MDA 120 may present options to: start or stop stimulation; increase or decrease the amplitude of the stimulation pulses (or adjust other pulse parameters and electrode settings); check the battery and operating status of the IMD; review data telemetered from the IMD; exit the MDA 120 and return to the mobile device's home screen (FIG. 4A), etc. The MDA 120, like other applications 110 selectable in the mobile device 100, may have been downloaded using traditional techniques, such as from an Internet server or an "app store."

When the MDA 120 is first selected and executed, or when an appropriate selection is made in the MDA (FIG. 4B), wireless communications with the IMD can be established using a communication means in the mobile device 100 and enabled by the MDA 120. The above-incorporated '518 patent discloses different examples in which such communication can occur, illustrated here in FIGS. 5A-5C.

In FIG. 5A, the MDA 120 establishes wireless communication directly with the mobile device 100 along RF link 75*b* using short-range RF communication means supported by the mobile device 100 (e.g., Bluetooth). In this instance, the IMD 10*b* would include short-range communication means compatible with RF link 75*b*, such as shown earlier with respect to FIG. 2B.

In FIG. 5B, a communication coil 112 in a communication head 113 is coupled by a cable 114 to a port on the mobile device 100, such as a USB port. In this instance, the communication coil 112 can be placed proximate to the IMD 10*a* to establish a magnetic induction link 75*a*, perhaps as modulated via FSK as mentioned earlier. The IMD 10*a* would include communication means compatible with magnetic induction link 75*a* (e.g., a coil antenna 24*a*), such as shown earlier with respect to FIG. 2A. The MDA 120 in this example would program the mobile device 100 to issue and receive data at its USB port, which data may be modulated or digital depending whether the modulation/demodulation circuitry resides in the mobile device 100 or the communication head 113.

In FIG. 5C, the mobile device 100 communicates with the IMD 10*a* via an intermediary bridge 90. The bridge 90 contains first communication means (including an RF antenna 118) for wirelessly communicating with the mobile device 100 via short-range RF link 75*b*, and second communication means (including a coil antenna 116) for wirelessly communicating with the IMD 10*a* via magnetic induction link 75*b*. The bridge 90, which is preferably battery powered, essentially "translates" short-range RF data on link 75*b* into magnetic-induction data on link 75*a*, and vice versa. The MDA 120 can thus program the mobile device 100 to use its short-range RF communication means (e.g., Bluetooth) even if the IMD is not compatible with such means, because the bridge 90 can translate and communicate with both.

The '518 patent further teaches that the MDA 120 can secure the mobile device 100 by controlling hardware and software in the mobile device that could affect, or worse corrupt, its use as an IMD external controller. For example, the '518 patent discloses that the MDA 120 upon execution can temporarily configure the mobile device 100 to prevent operation of the mobile device inconsistent with external controller functionality. In particular, the MDA 120 may disable or reconfigure hardware modules in the mobile device 100 that are either unnecessary or could potentially interfere with operation of the MDA 120, such as short-range communication means not used to communicate with the IMD, the camera, the cellular modem, GPS, the accelerometer, etc.

The MDA 120 can also terminate or temporarily suspend software tasks that might interfere with secure operation of the mobile device 100 as an external controller, such as other apps 110 displayable and executable from the mobile device home screen (FIG. 4A), or other software tasks that may run in the background of the mobile device in manners not immediately noticeable to the patient. Examples include e-mail and e-mail synchronization programs, software updates, alarm clocks, telephony functions, e-mail programs, music players, video games, mapping programs, Internet browsing applications, push service applications requiring Internet access, and other software tasks not essential to IMD communications.

The '518 patent additionally discloses that hardware and software security of these sorts can also be incorporated into the mobile device 100's booting process after it is powered on or restarted, or can modify the booting process to allow a patient to select how the mobile device 100 should be configured—either as a less-secure normal mobile device 100 or as a secure external controller for IMD communications.

While a mobile device 100 can function as an external controller for an IMD, the inventor sees certain problems that need to be overcome. For one, a mobile device 100 should be rendered operational to communicate with an IMD quickly. Assume for example that a patient's IMD is causing discomfort. It would be desirable for the patient to use the mobile device 100/MDA 120 (FIG. 4B) to quickly decrease the intensity of 1 MB stimulation, or to shut down operation of the IMD altogether. Mobile devices 100 may contain features preventing such quick operation, such as lock screens or other password protection mechanisms that require user input before the mobile device 100 can be operated as an external controller or otherwise. Additionally, the mobile device may have a series of menus or steps that must be navigated prior to running the MDA 120, even if the mobile device 100 is unlocked. If a patient is experiencing discomfort, having to take time to unlock the mobile device 100 or to navigate through menus would be aggravating at least, or at worst could injure the patient.

The inventor further recognizes that it is desirable to provide physical security regarding mobile device 100/IMD communications that is not wholly reliant on software. Even if an MDA 120 in a mobile device 100 is paired to a particular patient's IMD, another user of the patient's mobile device 100 could access the MDA 120 and potentially tamper with the patient's therapy. Alternatively, another user could download the MDA 120 to his mobile device 100 (even if not himself an IMD patient), and attempt to "hack" into a patient's IMD or the MDA 120 on the patient's phone. A physical security measure akin to a physical key for rendering a mobile device 100 useable as an 1 MB external controller is therefore desired.

Finally, while mobile devices 100 typically contain different types of communication means to enable various types of short-range wireless communications, the inventor realizes that it cannot be guaranteed that a patient's IMD will be compatible with such means. For example, if a patient has an IMD 10a containing an antenna coil 24a (FIG. 2A) operable in accordance with FSK, attempting to establish 1 MB communications using the mobile device 100's Bluetooth communication means would be ineffective, because the IMD is not compatible with Bluetooth. Conversely, it may be the mobile device 100 that is lacking in its communication ability. For example, while mobile devices 100 typically include common, commercially-used communication means (supporting Bluetooth, BLE, NFC, and WiFi for example), they may not be compatible with communication means used more-uniquely with implantable medical devices (such as Zigbee and MICS). This limits the utility of the mobile device 100 as an external controller for an IMD, particularly if it is desired to allow such devices to communicate directly (e.g., FIG. 5A).

BRIEF DESCRIPTION OF THE DRAWINGS

FIG. 1 shows an Implantable Medical Device (IMD) in accordance with the prior art.

FIGS. 2A and 2B respectively show cross sections of an IMD having a coil telemetry antenna and an RF telemetry antenna, in accordance with the prior art.

FIG. 3 show a dedicated external controller for communicating with an IMD, in accordance with the prior art.

FIG. 4A shows a graphical user interface of a mobile device, and FIG. 4B shows a graphical user interface of a Medical Device Application (MDA) on the mobile device for communicating with an IMD, in accordance with the prior art.

DETAILED DESCRIPTION

Disclosed is a plug-in accessory for operating a mobile device such as a mobile phone as an external controller for an Implantable Medical Device (IMD). In one example, the accessory includes a housing with a connector that can be inserted into a port on the mobile device, such as a coaxial audio port. Circuitry in the accessory can be powered by a battery, or by the mobile device, which can provide an audio power signal that the accessory can rectify for its power needs. An Accessory Application (AA) on the mobile device, which can comprise part of a Medical Device Application (MDA), works in conjunction with the accessory to configure the mobile phone for immediate use as an external controller. When the accessory is inserted into the mobile device's port, and optionally after a switch on the housing of the accessory is pressed, the AA operates to validate the accessory; to unlock the phone if necessary; to render the mobile device secure for use as an external controller; and to provide a graphical user interface on the mobile device to allow the patient to communicate quickly, easily, and securely with his IMD.

Communication with the IMD can occur using short-range communication means already typically present in the mobile device (e.g., Bluetooth), or the accessory can include such communication means, including one or more antennas and supporting telemetry circuitry compatible with the communication means supported by the IMD. This alternative is useful, in addition to other beneficial functionality provided by the accessory and the AA, in allowing a patient to use the graphical user interface on his mobile device to communicate with his IMD even if the mobile device doesn't have communication means compatible with that used in the IMD.

Figure 6:
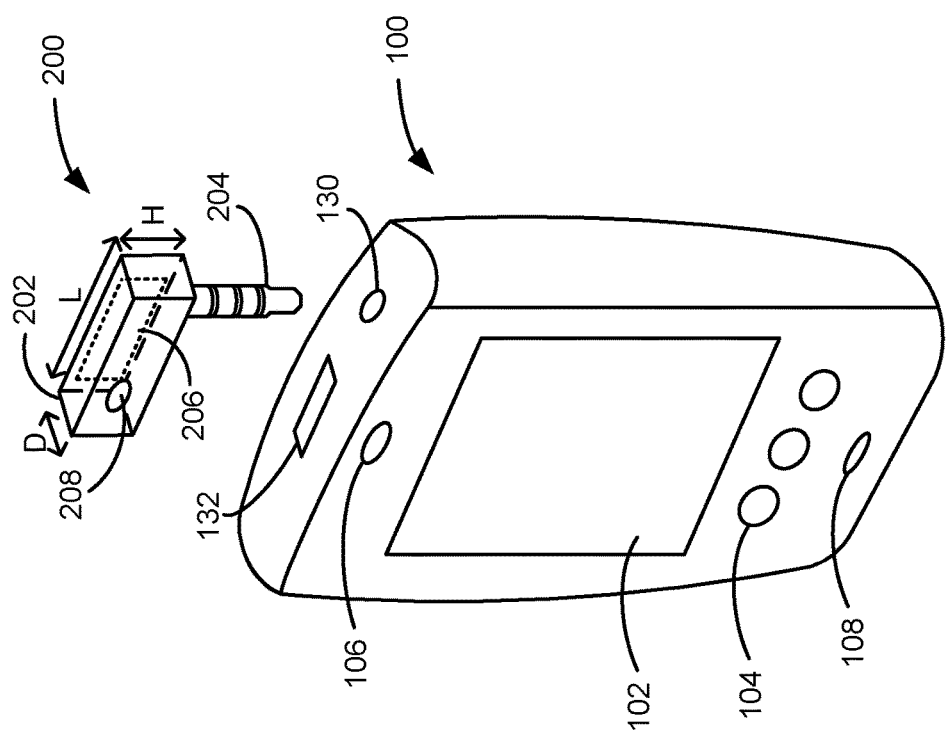
FIG. 6 shows a plug-in accessory to configure a mobile device to operate as an external controller for an IMD, in accordance with an example of the invention.

One example of a plug-in accessory 200 for render a mobile device 100 suitable for use as an external controller for an IMD, such as IMDs 10a and 10b discussed earlier, is shown in FIG. 6. As shown, the accessory 200 comprises a housing 202 formed of hard plastic for example. A printed circuit board (PCB) 206, which may be secured inside the housing 202 in a variety of well-known ways, is provided to integrate various electronic components in the accessory 200, which components are discussed subsequently. An optional switch 208, described further below, may be provided on the housing 202 and electrically coupled to the PCB 206. Switch 208 (if provided) may be recessed with respect to the housing 202 to avoid accidental triggering of the accessory 200.

The size of the accessory's housing 202 can vary depending on the sizes of its internal components it houses, and may also vary in accordance with the mobile device(s) 100 with which the accessory 200 is potentially useable. In this regard, it is preferred, although not necessary, that the accessory have a length (L) and depth (D) that does not exceed those of the mobile device 100. Additionally, the height (H) of the accessory is preferably as small as practical so as not to add significant additional height H to the mobile device 100 once the accessory is attached to the mobile device 100. Such sizing considerations render the accessory less obtrusive when coupled to the mobile device 100, which coupling is explained further below. In one example, the accessory has a length L of 25 mm or smaller, a depth of 10 mm or smaller, and a height H of 20 mm or smaller, although as just discussed such sizing is potentially dependent on different considerations.

The accessory housing 202 additionally supports a connector 204 electrically coupled to the PCB 206, which connector 204 is connectable to the mobile device 100. In the example shown, the connector 204 comprises a coaxial audio connector configured for receipt by an audio port 130 of the mobile device 100, which may otherwise normally be connected to a pair of headphones, a microphone, or a device having both of these functions. The connector 204 may comprise, for example, a 3.5 mm four-conductor TRRS (Tip Ring Ring Sleeve) connector for carrying a left audio output signal (L), a right audio output signal (R), an audio input signal (MIC), and a ground. Use of an audio coaxial connector 204 is preferred because mobile devices 100 almost universally have audio ports 130 of this type, regardless of the mobile device manufacturer or the operating system of the device. Use of an audio coaxial connector 204 also allows the mobile device 100 to provide power and to bi-directionally communicate data with the accessory 200, as discussed in detail below.

However, other types of connectors 204 coupleable to the mobile device 100 may be used with the accessory 200. For example, the accessory 200 could include a USB connector coupleable to a USB port 132 on the mobile device 100, which may also be used as a power port to charge the mobile device 100 from an AC power source (e.g., a wall socket).

As described further below, the accessory 200 operates to execute an MDA 120 as described earlier immediately upon its insertion into the audio port 130 on the mobile device 100, or when the optional switch 208 on the accessory 200 is pressed. As the mobile phone and DA 120 will still be used to control IMD communications, notice that the accessory 200 can completely lack a user interface, except perhaps for the optional switch 208. That being said, additional user interface elements (e.g., LEDs, or other switches) could be provided with the accessory 200 as well.

Figure 7A:
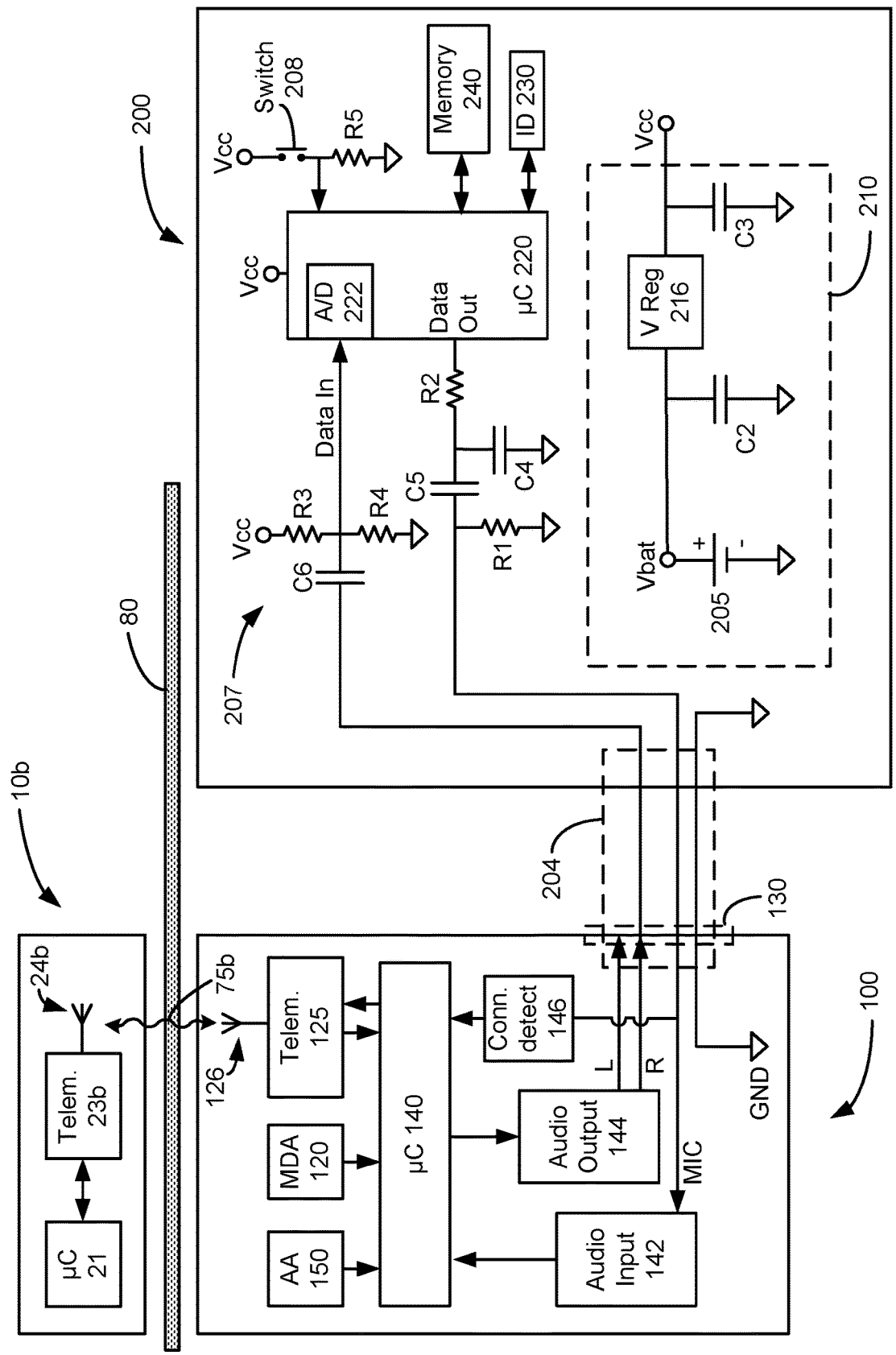
FIGS. 7A and 7B show examples of circuit diagrams for the accessory and the mobile device, which mobile device includes an MDA and an Accessory Application (AA), in accordance with examples of the invention.

FIG. 7A shows an example of the circuitry in the accessory 200 and circuitry and modules in the mobile device 100 implicated by the accessory 200. The mobile device 100 includes control circuitry such as a microcontroller 140, which controls the main functionality of the mobile device 100, and which has access to and can execute a number of different applications installed on the device, including the MDA 120 described earlier, and an accessory application (AA) 150, which comprises executable instructions written in accordance with the operating system running on the mobile device. AA 150 is discussed in further detail below.

The mobile device 100 further includes communication means—telemetry antenna 126 and telemetry circuitry 125—for allowing short range communications with other devices, and in this example also with an IMD 10b when the MDA 120 is executed. Such communication means can comprise components traditionally provided with commercial mobile devices for short-range RF telemetry for example, and thus may support Bluetooth or WiFi as common examples.

Figure 5B:
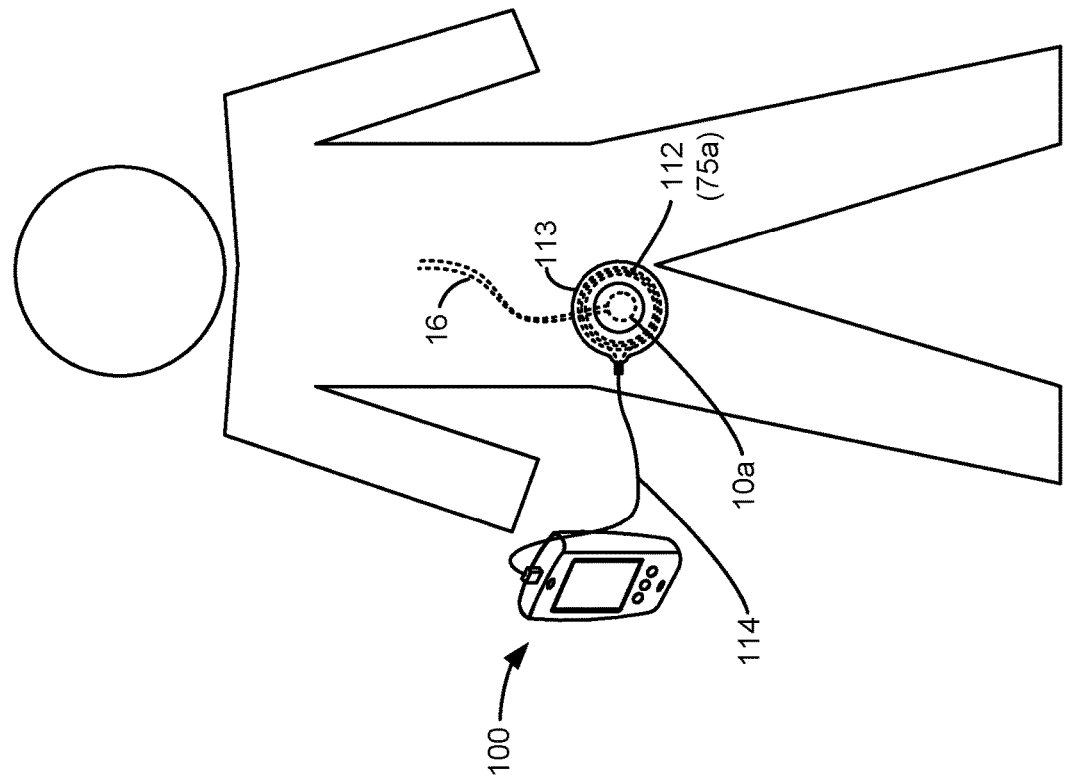
FIGS. 5A-5C show different manners in which a mobile device can wirelessly communicate with an IMD using the MDA of FIG. 4B, in accordance with the prior art.
Figure 5A:
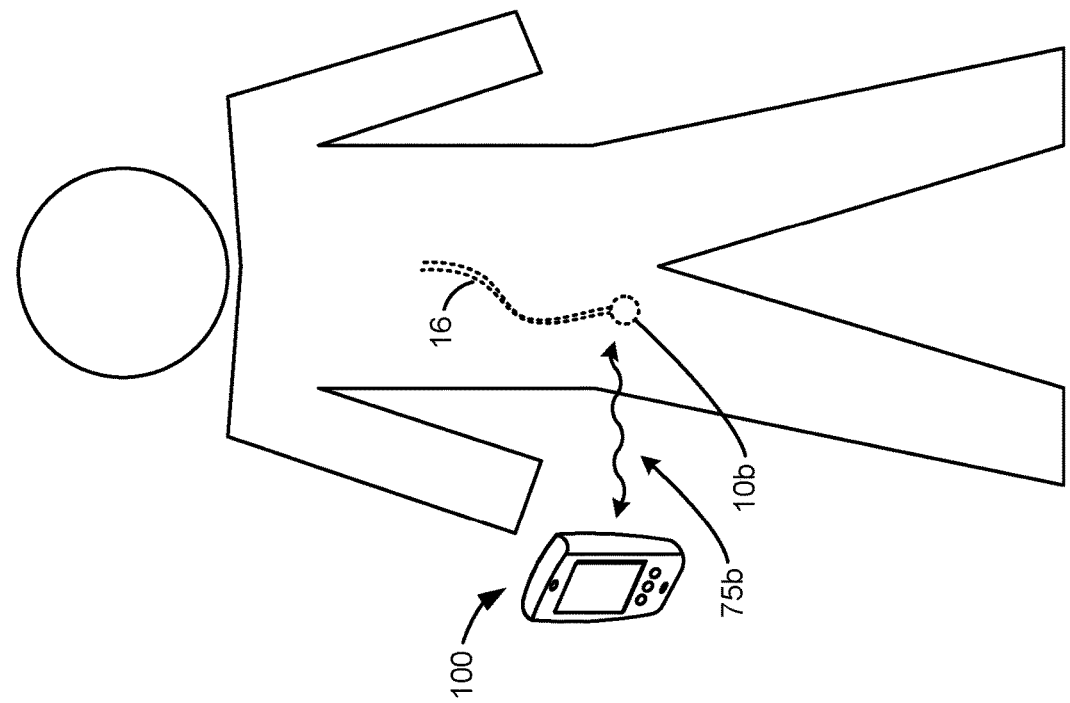
Figure 5C:
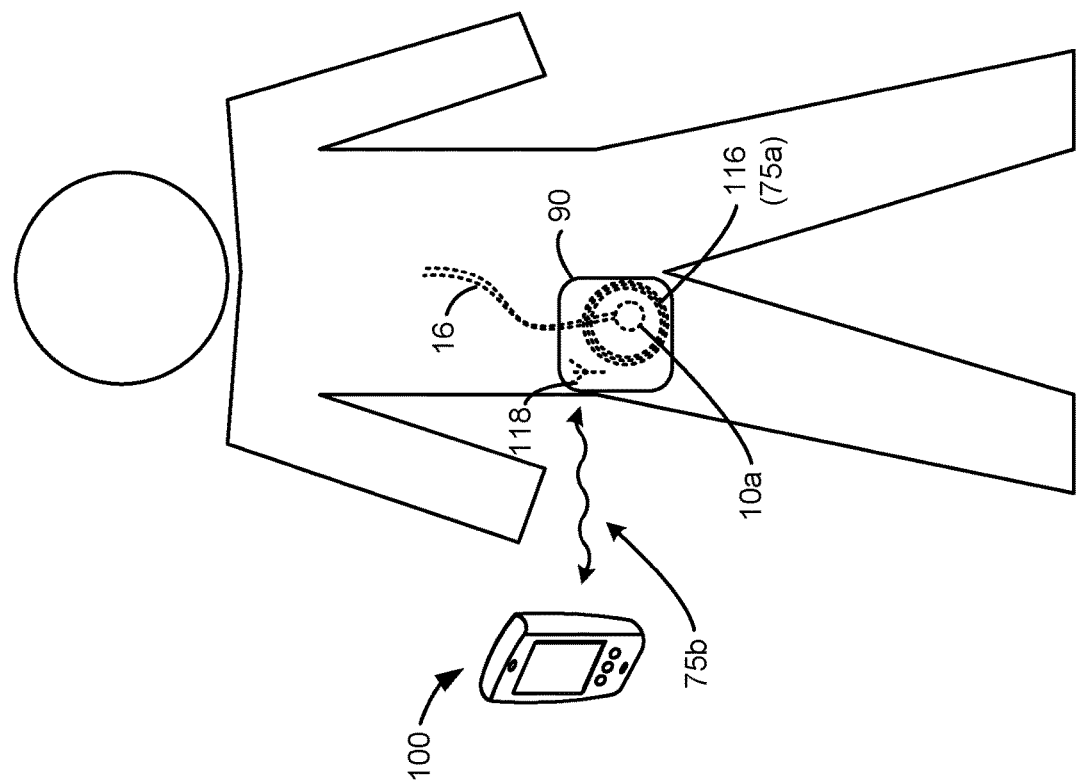
Figure 7B:
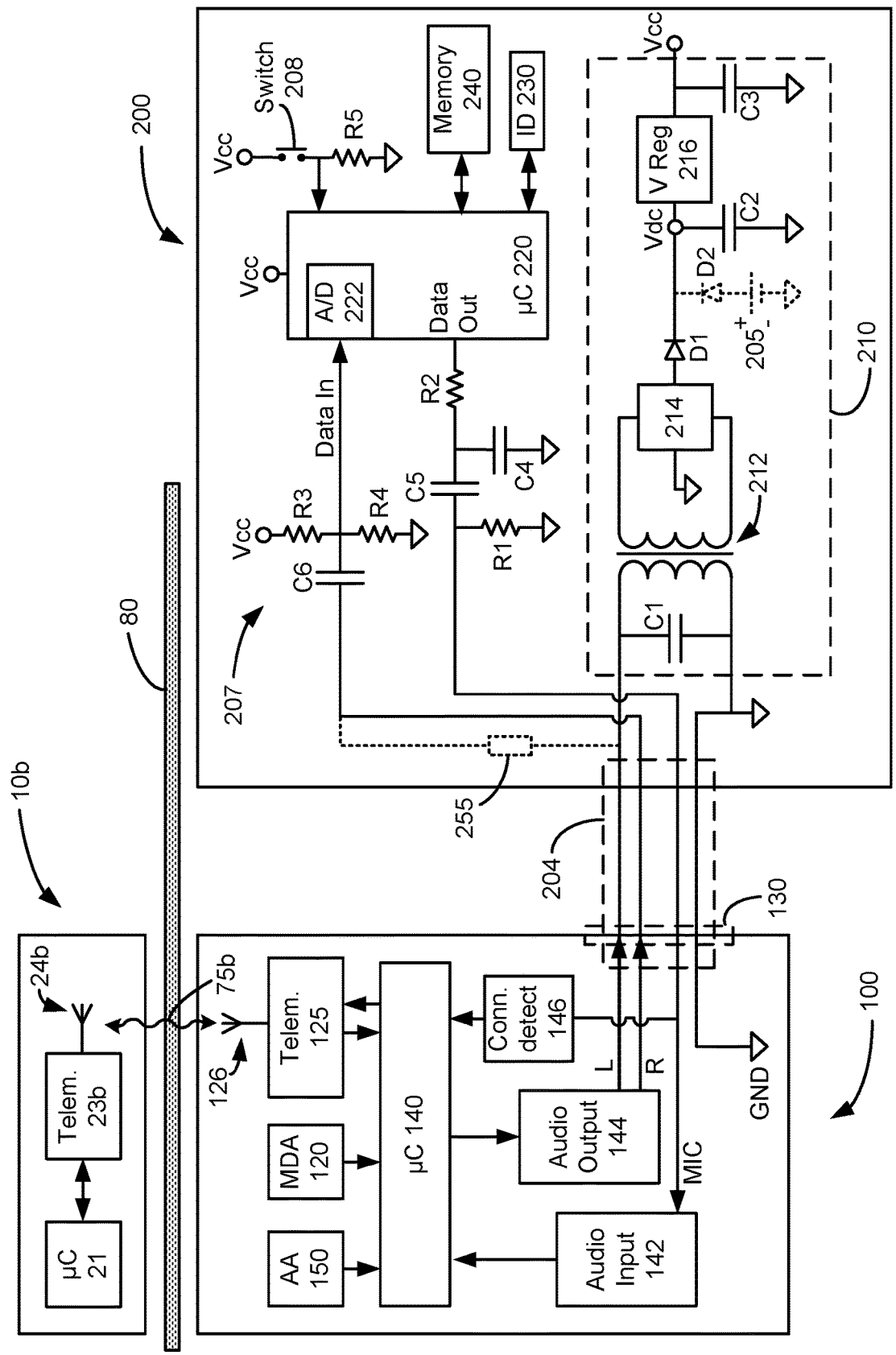

The mobile device 100's communication means may support communications with an IMD using any of the techniques discussed earlier with respect to FIGS. 5A-5C for example, although for simplicity FIGS. 7A and 7B illustrate direct communication between the mobile device RF antenna 126 via RF link 75b (as in FIG. 5A), which assumes that the IMD 10b includes compatible communication means, such as an RF antenna 24b (FIG. 2B). (Note that in the example of FIG. 5B coil antenna 112 in the communication head 113 would be used in lieu of RF antenna 126 in the mobile device 100). While the mobile device 100 may include additional communication means supporting different short-range RF standards, only 125 and 126 are shown as an example.

The mobile device 100 also includes audio input module 142, which is configured to receive an audio input (e.g., from a microphone; MIC) from the audio port 130, and an audio output module 144 to provide left and right audio outputs (L and R) to the audio port 130. A connector detection module 146 is used to detect when a connector (such as 204) has been inserted into the audio port 130.

The accessory 200 also includes control circuitry, again such as a microcontroller 220, which may receive an input from an optional switch 208 discussed above, which when pressed defeats pull down resistor R5 to provide a high logic (Vcc='1') input to the microcontroller. The microcontroller 220 may also have access to an accessory Identification Code (ID) 230, explained further below, and a non-volatile memory 240. (Modules 230 and 240 may also comprise a portion of the memory of the microcontroller 220). Power is supplied to the circuitry in the accessory 200 via a power supply voltage Vcc, which is in turn produced by power supply circuitry 210 in the accessory 200, which circuitry 210 can vary, as discussed further below.

The microcontroller 220 can communicate bi-directionally with the mobile device 100 using the connector 204 to which it is electrically coupled. In particular, the microcontroller 220 can receive data from the mobile device 100 using the audio output(s) L and/or R (only R is used in FIG. 7A), and can transmit data to the mobile device 100 using the audio input MIC. In accordance with the nature of these audio channels, such data transmissions are analog in nature, and can be formatted in a variety of manners, for example, using amplitude modulation, frequency modulation, or phase encoding schemes such as Manchester encoding (not shown). In accordance with the format chosen, the audio output module 144 can be configured to modulate data from the microcontroller 140 that is to be sent to the accessory 200 through the connector 204. Likewise, the audio input module 142 can be configured to demodulate data received from the accessory 200 through the connector 204 for interpretation by the microcontroller 140. Modulation and demodulation aspects can additionally be programmed into the microcontroller 140 itself, with audio input 142 and output 144 modules essentially acting as A/D and D/A converters.

Signal processing circuitry 207 in the accessory 200 assists in converting received analog signals from the connector 204 into a format interpretable by the accessory's microcontroller 220, and in converting digital data from the microcontroller 220 into analog signals suitable for transmission through the connector 204. Analog signals received from audio output R are AC-coupled to an input of microcontroller 220 via capacitor C6, with a voltage divider comprising resistors R3 and R4 used to adjust the DC offset of the signal (e.g., to Vcc/2 when R3=R4). Once the analog signal is so processed, it is preferably digitized for interpretation by the microcontroller 220, which may comprise use of an analog-to-digital (A/D) converter 222, which may be part of or separate from the microcontroller 220.

When transmitting data to the mobile device 100, resistor R2 and capacitor C4 smooth the digital output from the microcontroller 220 into a signal that is more analog in nature, which signal is then AC-coupled to the MIC audio input via capacitor C5. Resistor R1 in the accessory 200 is provided for the benefit of the connection detector 146 in the mobile device 100, which will recognize the insertion of the connector 204 into the audio port 130 upon sensing this resistance. Microcontroller 220 can be programmed to demodulate received data and to modulate data to be transmitted in accordance with the communication format chosen. With suitable programming, different communication formats and different modulation and demodulation schemes could be used for communications in different directions (audio output R; audio input MIC) through the connector 204.

In other examples in which the accessory's connector 204 is formatted to interface with a digital port of the mobile device, such as USB port 132, communications between the accessory 200 and the mobile device 100 can occur digitally. In this case, signal processing circuitry 207 in the accessory 200 would not be required.

In the example of FIG. 7A, power supply circuitry 210 includes a battery 205, such as a 3V CR1220 Lithium button cell battery. If necessary, a voltage regulator 216 (e.g., a low drop out regulator) can be used to regulate the battery voltage Vbat to the power supply voltage Vcc needed for the accessory's circuitry. This is not strictly necessary, and the circuitry can be driven directly by Vbat as well. Capacitors C2 and C3 can be used to smooth Vbat and Vcc respectively. If the battery 205 is replaceable, the housing 202 would include a hatch for battery access. Battery 205 may also be rechargeable, in which case it could receive power from a port in the housing (not shown). Alternatively, although not shown, battery 205 may be recharged by the mobile device 100 by an audio power signal received from the otherwise unused audio output L, as explained next.

In the example of FIG. 7B, the power supply circuitry 210 does not include a battery, but instead receives power from the mobile device 100. This occurs using the other of the audio outputs (L) not used to transmit data (R) to the accessory 200. For example, the audio output module 144 of the mobile device 100 may provide an audio power signal, such as a 4 kHz sine wave, on audio output L. This audio power signal is received at a transformer 212 in the power supply circuitry 210, which may have a winding ratio (e.g., 20:1) suitable to boost the voltage to a level suitable to derive the power supply voltage Vcc needed for the accessory 200. The resulting AC signal is provided to a rectifier 214, and passed through a backflow prevention diode D1, to create a DC voltage, Vdc. As before, this voltage can be regulated (216) to Vcc, with capacitors C2 and C3 used to smooth Vdc and Vcc respectively.

FIG. 7B additionally shows modifications in dotted lines. For example, power supply circuitry 210 may optionally include a battery 205, similar to FIG. 7A. As shown, the battery 205 can provide an optional voltage to Vdc through back flow prevention diode D2, thus allowing the regulator 216 to receive power from either the rectifier 214 or the battery 205, depending on which outputs a larger voltage. (Diodes D1 and D2 can comprise Schottky diodes to reduce their threshold drops).

In another modification, data may be sent from the mobile device 100 to the accessory 200 using the same audio output used to provide the audio power signal. This is shown in FIG. 7B using audio output L, which carries both the audio power signal for the transformer 212 and (as represented by the dotted line) data to be received by the microcontroller 220. (Audio output R may thus not be used in this example). In this example, the signal processing circuitry 207 may include a filter 255, e.g., a notch filter, to remove the frequency of the audio power signal (e.g., 4 kHz) from the data. Otherwise, the audio power signal may be digitally filtered in the microcontroller 220 to recover the data.

If means other than audio port 130 are used to connect the accessory 200 to the mobile device 100, power may be provided to the accessory 200 in a different fashion. For example, if the accessory 200 includes a USB connector connectable to USB port 132 on the mobile device 100, the accessory 200 can receive power via the USB-dedicated power pin in the port 132.

With the accessory 200 and means of communicating with the mobile device 100 explained, attention returns to use of the accessory 200 to execute the MDA 120 on the mobile device 100 to allow a patient to communicate with his IMD. As noted earlier, an accessory application (AA) 150 can accompany the MDA 120 in the mobile device 100, and can be downloaded to the mobile device 100 in similar fashion. AA 150 and MDA 120 may also be integrated into a single MDA application, with the AA portion operating in that application before it presents the MDA home screen (FIG. 4B). AA 150 may additionally comprise a single stand-alone application, or a number of different applications, software programs, or instructions working together, or pieces of such executable structures. Nonetheless, for convenience the AA 150 is described separately from the MDA 120 so that their separate functions can be better appreciated.

AA 150 is designed to determine when a device has been plugged into the mobile device 100 and to validate such a device as an accessory 200, and so the AA can comprise one or more validation instructions executable in the mobile device for this purpose. The AA 150 can optionally configure the mobile device 100 to render it secure for operation as an external controller for the IMD, and to remove impediments in the mobile device 100 to external controller operation, such as by defeating screen locks or other protection measures operating on the mobile device 100. Thus, AA 150 can additionally comprise one or more mobile device preparation instructions executable in the mobile device to affect such functionality. After validation of the accessory 200, the AA 150 can execute the MDA 120, and so additionally comprises one or more MDA launch instructions executable in the mobile. The mobile device preparation instructions may be included within the MDA 120 instead of the AA 150, and may execute first in the MDA 120 before presentation of the MDA home screen (FIG. 4B).

In preferred embodiments, the AA 150 is pre-paired with a particular accessory 200, such that the AA 150 will only operate to execute the MDA 120 after that accessory is validated by the AA 150. This can occur using the accessory ID 230 programmed into the accessory 200. A unique accessory ID 230 may be programmed into each accessory 200 by its manufacturer, for example, in flash memory, using programmable fuses or antifuses, DIP switches, by wire/solder bonding, etc. The accessory ID 230 may also be programmable after accessory 200 manufacture, and may be set to match the ID of the IMD that the MDA 120 will control. Accessory ID 230 may also be provided by the AA 150.

The accessory 200 can provide the accessory ID 230 to the mobile device 100 and the AA 150 via the audio input (MIC) as part of the validation procedure. Accessory ID 230 may also be encrypted, in which case it would be decrypted by the AA 150 in accordance with the encrypting method used, of which there are many. Upon validation of the accessory ID 230 by the AA 150, the AA 150 may transmit a reply (again, possibly encrypted, and possibly including an ID for the mobile device 100 or the AA 150) to the accessory 200 to inform its microcontroller 220 that communications with the AA 150 may commence. Although not shown, the accessory 200 may provide as part of the validation procedure an indication to the AA 150 that it has sufficient power to operate, and thus power supply monitoring circuitry may be included in the accessory 200 (not shown).

Figure 8:
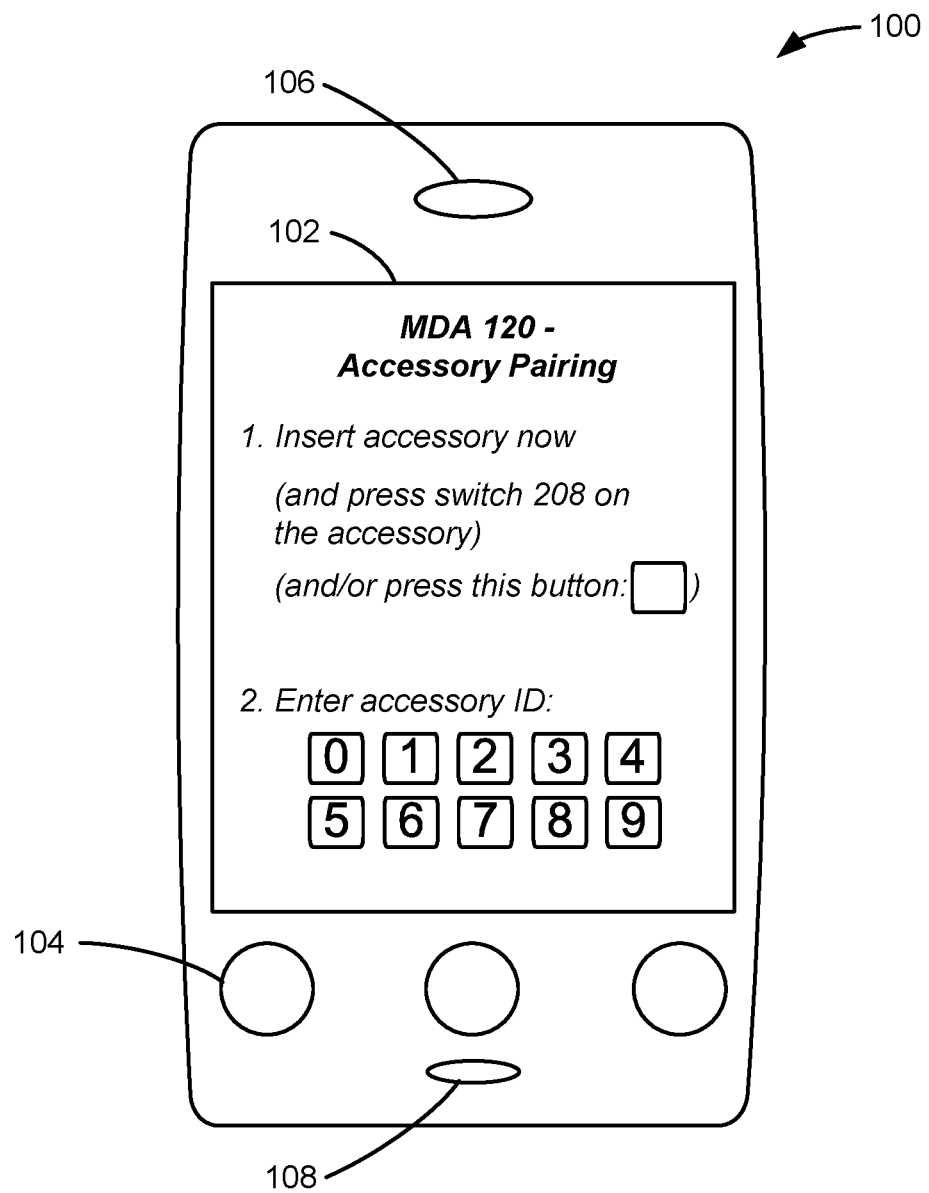
FIG. 8 shows a graphical user interface provided by the MDA or the AA for pairing a particular accessory to the AA in the mobile device, in accordance with an example of the invention.

Pairing of the AA 150 and a particular accessory 200 can occur in different manners, which may occur using the MDA 120. The MDA 120, when first run or upon making a suitable menu selection, can provide different pairing options to the patient, as shown in FIG. 8. In a first example, the patient can be instructed to insert her accessory 200 into the audio port 130. The MDA 120 may then read the accessory ID 230, or perhaps require other steps, such as pressing the switch 208 on the accessory 200 (if present), or pressing a button on the mobile device 100. In a second example, the accessory ID 230 for a patient's accessory 200 can be provided to her in some other secure fashion (by mail, by accessing the manufacturer's website with a password, etc.), which the patient can then type into the MDA 120. For example, a manufacturer website may instruct the patient to type in the accessory 200's serial number, after which the website can provide the accessory ID 230 to the patient. In a third example, an accessory ID can be provided with each AA 150 version, which is initially uploaded and stored in the accessory 200 (in 230) and provided from the accessory 200 to the AA 150 during subsequent validations. Once the accessory ID 230 is read or input, it can be provided by the MDA 120 to the AA 150 to allow for subsequent validation of the accessory 200 by the AA 150 without the MDA 120's assistance. Pairing may also occur under the control of authorized personnel such as the manufacturer or the patient's clinician.

Pairing of AA 150 and accessory 200, and subsequent validation of the accessory 200 by the AA 150, does not necessarily require the AA 150 to consider just a unique ID 230 of particular accessory 200. Instead, the AA 150 may be designed to simply validate the device as a compliant medical device control accessory 200, regardless of which particular one it is. In this regard, the control circuitry 220 in the accessory 200 may provide to the AA 150 any form an accessory validation information 230 that the AA 150 can review to validate an inserted device as a medical device control accessory 200, as opposed to some other device inserted into the port 130.

For example, accessory validation information 230 may comprise the model number of the accessory 200, which would be the same from patient to patient. Alternatively, accessory validation information 230 may not comprise data (e.g., bits) per se, but could instead comprise some other form of information that differentiates the medical device control accessory 200. For example, accessory 200 could provide unique signals of particular shapes, frequencies, or voltages recognizable by the AA 150. Resistance R1 (FIG. 7A), generally used by the connection detection module 146 in the mobile device, could have a particular value indicative of the medical device accessory 200, etc. Such modifications would be beneficial as it would allow a patient to use another patient's accessory 200 if necessary, or to allow the manufacturer to simply provide a new accessory 200 to a patient if it has been lost. Pairing steps may not be necessary, as the AA 150 can be programmed with the accessory validation information 230 in mind, and thus be able to validate any accessory 200 that it later receives. Despite such alternatives, the below discussion assumes use by the AA 150 of accessory IDs 230 to validate an accessory 200.

Figure 9A:
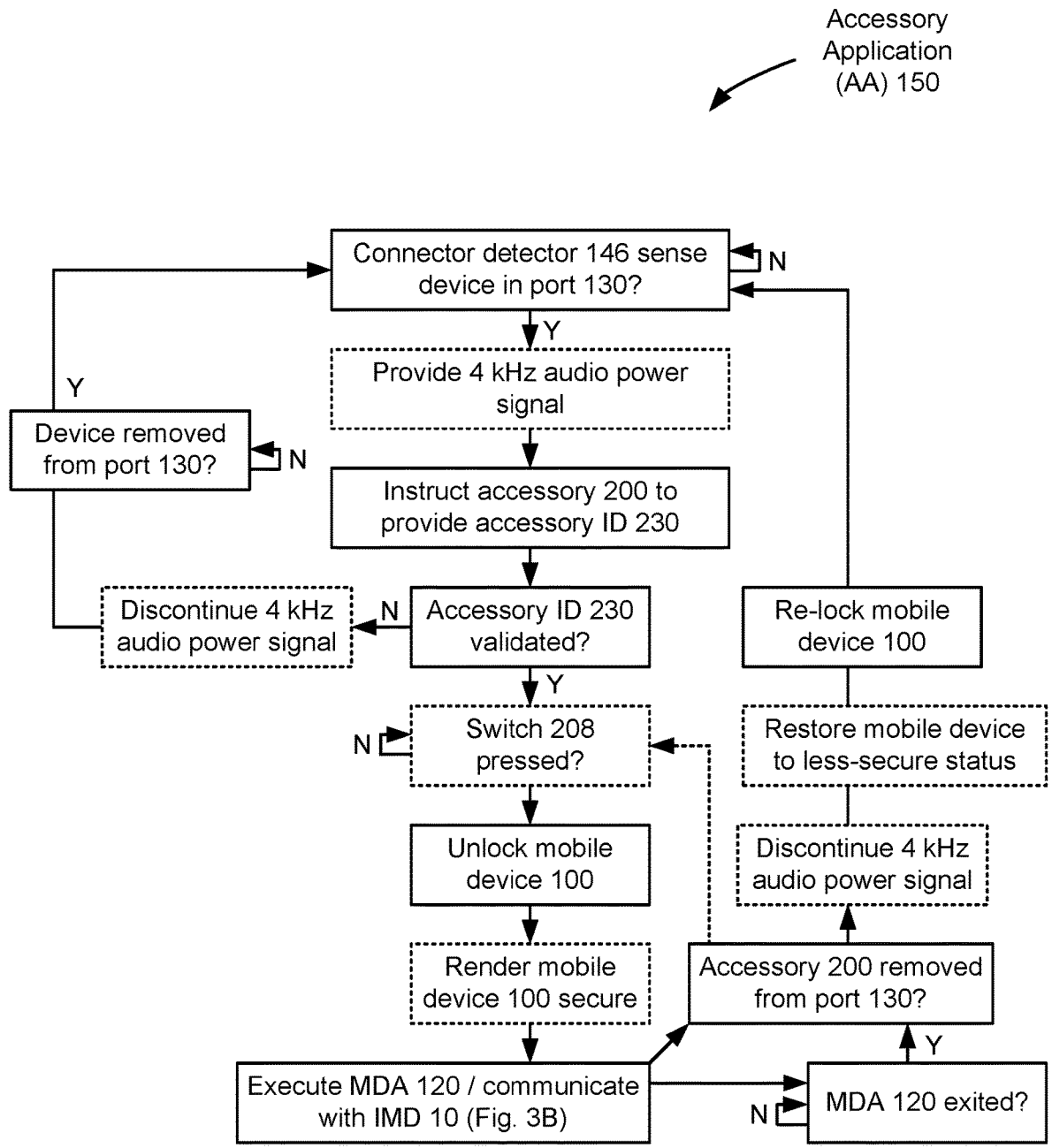
FIGS. 9A and 9B show example flow charts illustrating operation of the AA, in accordance with examples of the invention.

How the AA 150 operates depends on the means by which the accessory 200 is powered—i.e., whether the AA 150 must take steps to power the accessory 200—and whether activation of the accessory 200 by the patient (via switch 208) is required. FIG. 9A depicts a first example of an AA 150 in which the AA 150 instructs the accessory 200 to transmit its accessory ID 230 without the need for the patient to press switch 208.

In a preferred embodiment, the AA 150 once installed on the mobile device 100 operates continuously, periodically polling the connector detection module 146 to determine whether it has detected the insertion of a device into the audio port 130 (or other port if the accessory 200 is configured with a different connector, such as a USB connector). If a device is detected, the AA 150 can execute at least one power instruction to provide a 4 kHz audio power signal (e.g., on audio output L; FIG. 7B) if the accessory 200 is reliant on the AA for power—for example, if accessory 200 lacks a battery 205 or is not coupled to a port on the mobile device 100 that readily provides power (such as USB port 132). If the accessory 200 by contrast is independently powered, the AA 150 need not concern itself with providing power to the accessory, and this step can be skipped.

Once a device is detected at the audio port 130 (and powered if necessary), the AA 150 instructs the device to provide its accessory ID 230, e.g., using one of the audio outputs (e.g., R in FIG. 7A). In response to this instruction, the accessory 200 transmits its accessory ID 230 to the mobile device 100 for interpretation by the AA 150, e.g., using the audio input MIC. If a device other than the accessory 200 has been inserted into the audio port 130 (e.g., a pair of headphones), that device would most likely not understand the instruction, and thus would provide no data to the AA 150 in return.

A short time after transmitting the instruction, the AA 150 attempts to validate the accessory ID 230, as described earlier. If such validation is not successful, either because the accessory ID 230 does not match that paired to the AA 150, or because no data was received from the device, validation of the device as the accessory 200 fails. The AA 150 may alternatively send the instruction some number of additional times before determining that validation has failed. At this point, the AA 150 can discontinue provision of the audio power signal (if it was provided), and can otherwise wait for the device (whatever it may be) to be removed from the audio port 130, as reported by connector detection module 146. Once the device is removed, AA 150 can return to waiting for another device to be inserted into audio port 130 in the future.

Notice in this example that the time from device insertion into the audio port 130 until its accessory validation or failure of validation can be quick, and perhaps not perceptible to the patient. This is preferred especially if an audio power signal is provided: if the patient inserts an actual audio device (e.g., headphones) into the audio port 130, the audio power signal should be quickly discontinued after failure of accessory ID validation. In this way, the patient is not bothered by hearing the audio power signal with his other devices, which can otherwise be used normally with the mobile device 100.

Once these validation instructions have been executed, and if validation is successful, the AA 150 can optionally wait for the patient to press the switch 208 on the accessory 200 to automatically execute the MDA 120. This can occur by providing an instruction from the accessory 200's microcontroller 220 to cause the AA 150 to in turn execute an MDA launch instruction to execute the MDA 120. However, this step may not be necessary, and instead mere insertion of a valid accessory 200 can signal the patient's desire to the AA 150 to execute the MDA 120, in which case a switch 208 on the stop accessory 200 may not be necessary, as noted earlier.

After validation (or after the optional switch 208 press), the AA 150 continues and may issue one or more mobile device preparation instructions. Such instructions can include unlocking the mobile device 100 if necessary, which can occur in different manners. Because the AA 150 is preferably written with different mobile device operating systems in mind (e.g., iOS, Android, Windows mobile, etc.), it can know the instructions necessary to automatically unlock the device without user input.

Alternatively, data necessary to unlock the mobile device 100 (patient passwords for example) can be stored in the mobile device 100 and retrieved by the AA 150, or can be stored in the accessory 200, for example, in memory 240. If stored in the accessory 200, the AA 150 can instruct the accessory 200 to automatically provide such unlocking data, similar to the manner in which it receives the accessory ID 230. Note that unlocking data can be written by the AA 150 to the memory 240 in the accessory 200 during an earlier communication session. Alternatively, writing unlocking data to the accessory 200 can be presented as an option to the patient on the MDA home screen, akin to FIG. 8 (although not shown). The accessory 200 may alternatively contain other forms of validation that the AA 150 can query before unlocking the mobile device 100, such as an indicator bit set by the patient to control whether automatic unlocking is to take place.

In a next optional step, the AA 150 can execute further mobile device preparation instructions to render the mobile device 100 secure for use as an external controller for the IMD, as disclosed in the above-incorporated '518 patent discussed earlier. Thus, the AA 150 may operate to disable or reconfigure certain hardware modules in the mobile device 100, and/or terminate or temporarily suspend certain software tasks. For example, other applications running in the mobile device 100 may be shut down, and Bluetooth links connected to other non-IMD devices (e.g., a headset) can be disconnected to allow the MDA 120 to use this Bluetooth link (for example) to communicate with the IMD. Note that such mobile device preparation instructions may instead optionally comprise initial instructions undertaken by the MDA 120 after it is launched.

At this point, the AA 150 can execute the MDA launch instruction, which causes the MDA 120 to execute. As such, the MDA's home screen (FIG. 4B) may be immediately presented to the patient, who can begin communicating with and adjusting the settings of her IMD.

Note in this example of FIG. 9A that presentation of the MDA home screen could occur essentially immediately upon insertion of the accessory 200 into the audio port 130 (particularly if the optional switch 208 pressing step is not used between validation and execution of the MDA 120) because all of the steps are electronically automated. No user input to the mobile device 100 is required, such as unlocking and menu navigation, and thus the patient can quickly access and control IMD therapy, which is beneficial for the reasons discussed earlier. The AA 150 preferably continues to operate when the MDA 120 is operating so that the AA 150 can execute one or more exiting instructions after IMD communications using the MDA 120 are complete, as discussed next.

Once the patient is done communicating with the IMD, she may exit the MDA 120 (see FIG. 4B), or remove the accessory 200 from the audio port 130. Until the accessory 200 is removed, the AA 150 may continue to monitor whether the switch 208 (if present) has been pressed (even if not pressed initially), in which case the MDA 120 can be executed again (perhaps preceded again by preparatory unlocking or optional securing of the mobile device 100). Otherwise, once the accessory 200 is removed, the AA 150 can discontinue issuing of the audio power signal (if it was provided), and return the mobile device 100 to its status prior to accessory ID validation. For example, hardware modules can be re-enabled or configured to their original less-secure statuses, and software tasks that were suspended can be reinstated, as discussed in the '518 patent. If the mobile device 100 had been automatically unlocked by the AA 150 as described earlier, it can be re-locked. The AA 150 can then return to its beginning to assess the insertion of a future device into audio port 130.

Although not shown in FIG. 9A, notice that the audio power signal could have been discontinued earlier in the process after the accessory 200 had provided all data necessary to the AA 150, for example, its accessory ID 230, unlocking data, etc. Likewise, the accessory 200 could be removed from the audio port 130 at such stages.

Figure 10:
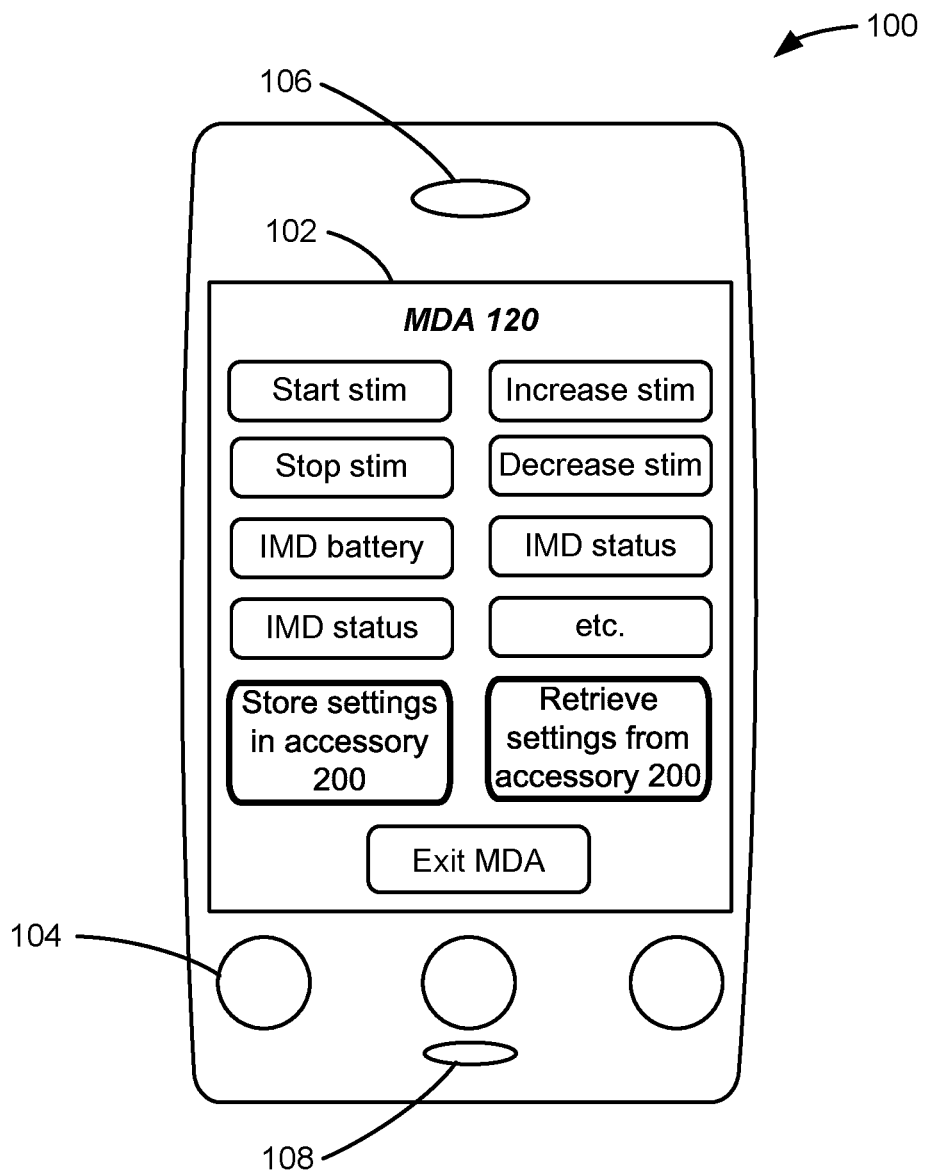
FIG. 10 shows a graphical user interface provided by the MDA for allowing a stimulation program to be stored in or retrieved from the accessory, in accordance with an example of the invention.

However, powering the accessory 200 continuously while inserted in the audio port 130 (if necessary), and requiring the accessory 200 to remain inserted in the audio port 130 during use of the MDA 120, is preferred to allow free communication between the AA 150, the MDA 120, and the accessory 200. This allows the accessory 200 to optionally provide additional functionality to the MDA 120, as shown in FIG. 10. For example, patient therapy settings prescribed by the MDA 120 for execution by the IMD or other patient-specific data can be stored in accessory 200 (e.g., in memory 240) as a stimulation program, and thus can be read back into the MDA 120 later, using options provided in the MDA. Although not shown, such stored stimulation programs could also be named to indicate particular patient activities with which they are associated (sitting, sleeping, etc.), making their later retrieval more intuitive. The patient can then transfer these stimulation programs stored in the accessory 200 to a new mobile device 100 onto which MDA 120 and AA 150 have also been downloaded, and which is also capable of communicating with the 1 MB (such as another mobile phone of the patient, the patient's iPad, etc.). Thus, such stimulation programs or other patient-specific data can be quickly selected and used to control the IMD via the MDA 120 in the new device (perhaps after AA 150/ accessory 200 pairing as described earlier).

Memory 240 can be used to store other useful data as well, such as present or historical data regarding patient control of the IMD via the MDA 120. Additionally, data telemetered from the 1 MB to the mobile device 100 (e.g., electrode resistances, 1 MB battery voltage, IMD operation or failure codes, temperature data, etc.) can also be stored in the accessory 200, thus allowing such present or historical data to be transferred and reviewed on other mobile devices 100 or computer devices having similar ports (e.g., 130) into which the accessory 200 can be inserted.

Requiring the accessory 200 to remain in the port 130 in the mobile device 100 during MDA 120 operation also ensures that patient therapy cannot be changed or tampered with (e.g., by a user of the patient's mobile device 100, or by a user who has downloaded the MDA 120 to his mobile device, but who doesn't have access to the accessory 200), therefore providing a physical means of securing IMD control. In fact, to prevent tampering with the MDA 120 (even when it is not being used), it is preferred to require a patient to insert and validate his accessory 200 before the MDA 120 (or AA 150) can be updated or changed on the mobile device 100, via an Internet app store for example. That is, the MDA 120 (or AA 150) data structures (files) may be locked on the mobile device 100, and only updatable if the accessory 200 is attached and preferably validated, as determined by the AA 150.

Figure 9B:
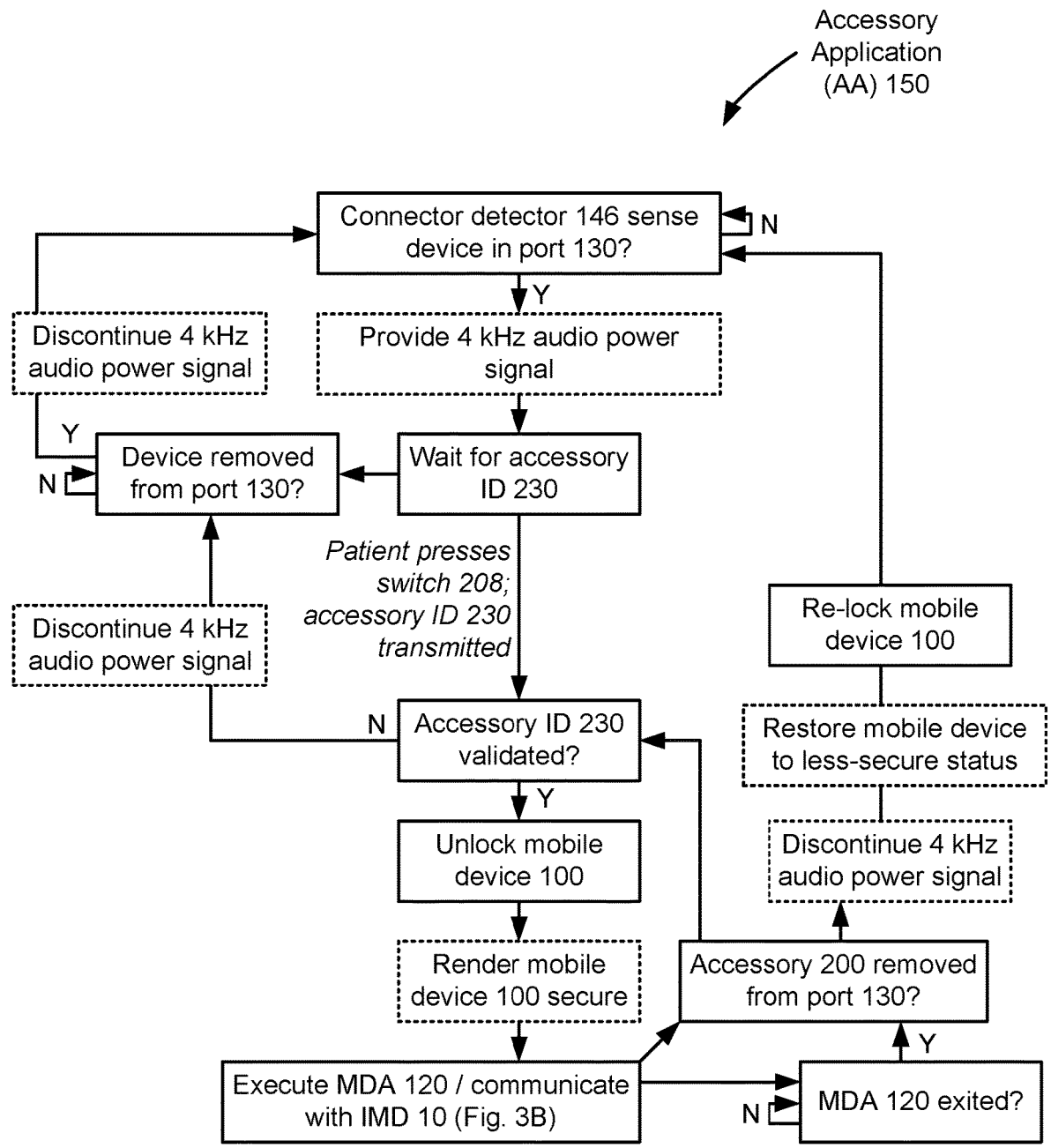

FIG. 9B shows another example of the AA 150 which waits for a patient to activate the accessory 200, for example by pressing switch 208, before the accessory 200 is validated and the MDA 120 executed. Many of the steps in FIG. 9B are similar to those already discussed in FIG. 9A, and are not repeated in detail.

Upon detecting the insertion of a device into audio port 130, AA 150 can again optionally power the accessory if necessary, but then waits for data from the accessory 200. In this example, the patient presses the switch 208 on the accessory 200 after inserting it into the audio port 130 on the mobile device 100. Pressing the switch 208 instructs the microcontroller 220 in the accessory to transmit the accessory ID 230 to the mobile device, e.g., along audio input MIC. This accessory ID 230 may be transmitted continuously or at least until the AA 150 acknowledges its receipt via audio output R. AA 150 may be programmed to wait for a validation period after the accessory 200 is inserted, which period can be consistent with how long it would be expected for a patient to press switch 208 after inserting the accessory 200, such as up to five seconds. If the AA 150 cannot validate the accessory ID 230 within the period, it may assume some device other than the accessory 200 has been inserted into the audio port 130, and may discontinue the audio power signal (if it was provided). As before, the AA 150 can wait to return to its beginning until the unknown device is removed from the audio port 130. If not discontinued earlier, the optional audio power signal can be discontinued at this point before the AA 150 returns to its beginning.

If the patient has pressed the switch 208 to transmit the accessory ID 230, and if it is validated by the AA 150, the AA 150 can again take steps to prepare the mobile device 100 for MDA 120 operation, such as the unlocking and optional securing steps discussed earlier. Thereafter, the MDA 120 is executed by the AA 150, and the patient can communicate with her IMD. As before, the patient can exit the MDA 120 or remove the accessory 200 from the audio port 130, which will discontinue the audio power signal, restore the mobile device 100 back to its less-secured original state, re-lock the mobile device 100, and return the MDA 120 to its beginning. If the accessory 200 is not removed, the AA 150 can continue to monitor for another switch 208 press, and execute the MDA 120 again if necessary. As before, the accessory 200 can be unpowered or removed earlier in the process, but this is not preferred for the reasons discussed with respect to FIG. 9A.

As noted in the Background, it cannot be guaranteed that a patient's IMD will be compatible with the communication means built into a commercial mobile device 100 potentially useable as an IMD external controller. Two examples illustrate such incompatibility.

In a first example, a mobile device 100 may have for example Bluetooth or WiFi communication means (e.g., telemetry circuit 125 and antenna 126 in FIG. 7A), while an IMD 10a may have magnetic-induction communication means (e.g., telemetry circuitry 23a and antenna coil 24a in FIG. 2A), which together are incompatible to establish either a magnetic induction link 75a or a RF link 75b between the two devices 100 and 10a.

In a second example, an IMD 10b may have for example MICS communication means operable at 402-405 MHz (e.g., short-range RF telemetry circuitry 23b and short-range RF antenna 24b in FIG. 2B). Although the mobile device 100 (supporting Bluetooth, WiFi) and the IMD 10b (supporting MICS) in this second example both support short-range RF communications, the differences in their communication means prevents the establishment of an RF link 75b between them.

To address such potential incompatibilities between the communications means in the mobile device 100 and the IMD, a modified accessory 300 can include communication means—antenna 302 and telemetry circuitry 301—compatible with the IMD's communication means. The mobile device 100 to which accessory 300 is connected can as before include AA 150 and MDA 120, which can operate in the various manners already discussed. Thus, the accessory 300 can be verified by AA 150 and MDA 120 executed render a graphical user interface on the mobile device 100 (FIG. 4B) to enable communications with the IMD, although communications with the IMD would use the accessory 300's communication means instead of the incompatible communication means in the mobile device 100. Note that while the accessory 300 ultimately acts as the IMD communication means, the mobile device 100 is still used to provide a graphical user interface to control IMD communications, and thus the accessory 300 still remains relatively simple and can lack significant user interface elements.

Figure 11B:
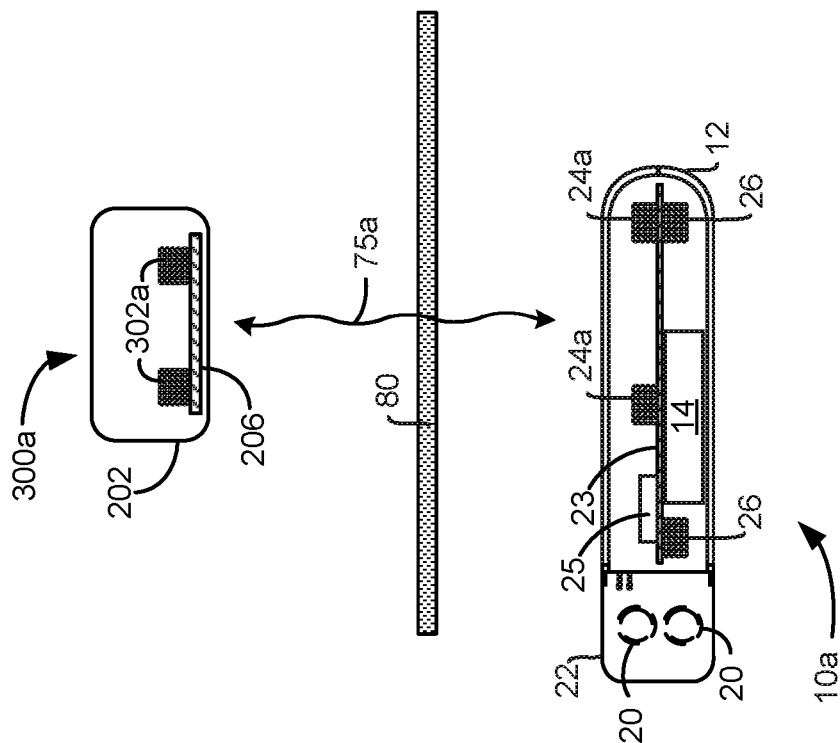
FIGS. 11A-11C show a modified accessory for a mobile device having a magnetic-induction antenna for communicating with an IMD in lieu of the mobile device's communication means, in accordance with an example of the invention.
Figure 11A:
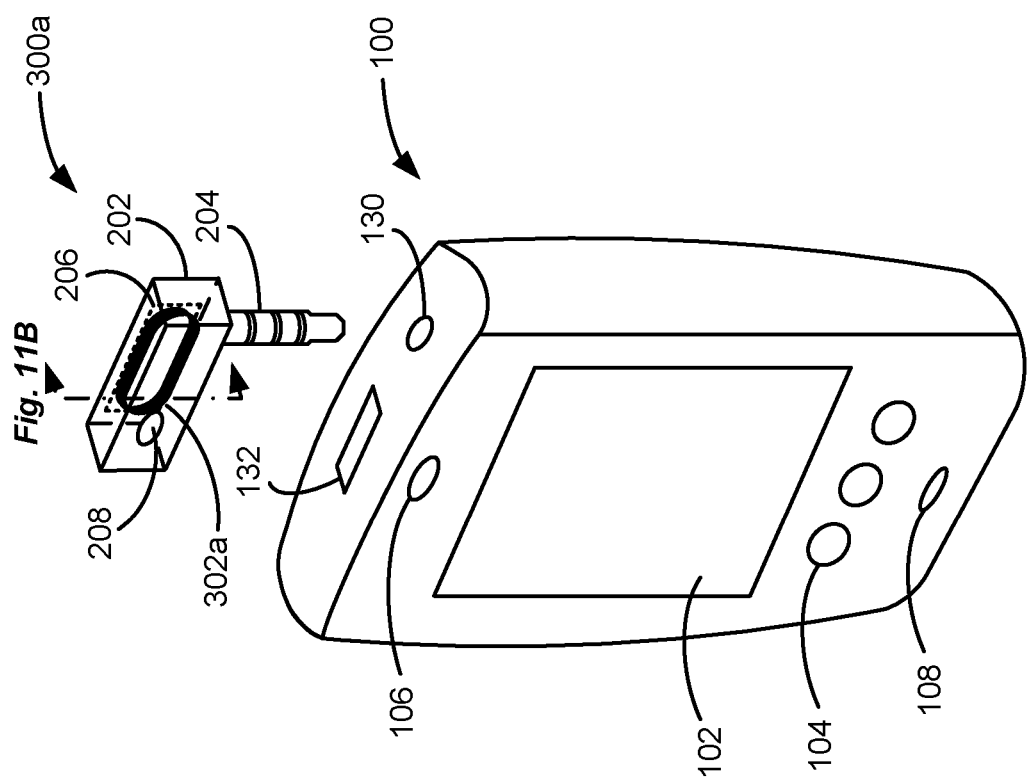
Figure 11C:
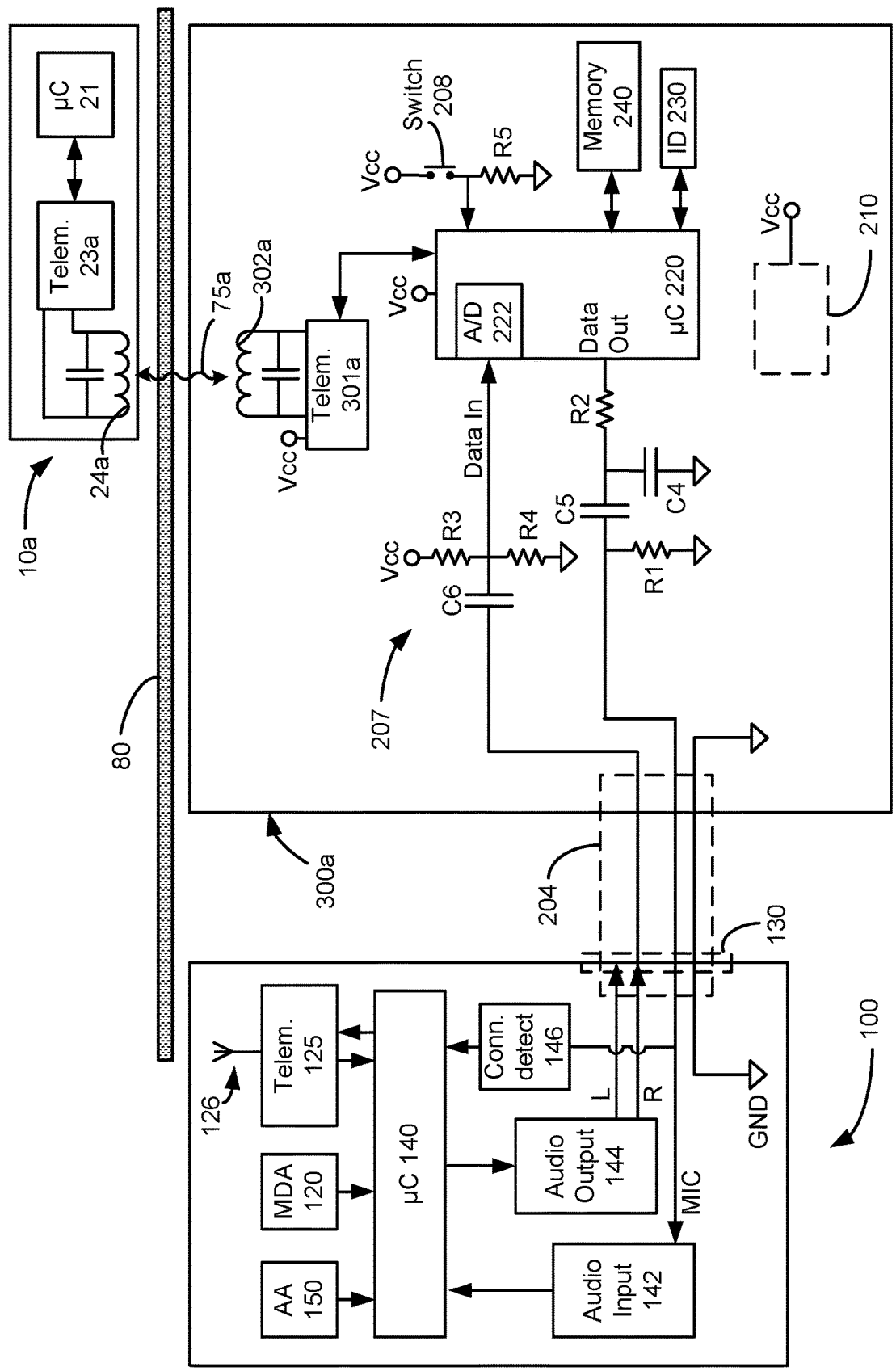

FIGS. 11A-11C show an example of an accessory 300 (300*a*) addressing the first example described above, in which the IMD 10*a* includes magnetic-induction communication means (FIG. 2A) operating for example using FSK communications as described earlier. To be compatible with IMD 10*a*'s communication means, the accessory 300*a* contains an antenna coil 302*a* and telemetry circuitry 301*a* also operable using the same FSK scheme. The antenna coil 302*a* and telemetry circuitry 301*a* are coupled to the PCB 206 in the accessory 300*a* along with other components illustrated in FIG. 11C and discussed earlier. Telemetry circuitry 301*a*, like microcontroller 220, is powered (Vcc) by the power supply circuitry 210 as described earlier (FIGS. 7A, 7B).

The antenna coil 302*a* can be secured in the housing 202 in any number of ways, and may proceed around the periphery of the PCB 206 as shown in FIGS. 11A and 11B (in cross section). Other accessory components (including telemetry circuitry 301*a*) can be affixed to the PCB 206 within the area of the antenna 302*a*. However, there are many different manners in which the antenna coil 302*a*, PCB 206, and its components can be arranged within the housing 202. Although not shown in FIG. 11B, antenna coil 302 may be positioned on bottom of the PCB 206 facing the IMD 10*a*, while other accessory components are mounted on the top of the PCB 206. Note that the example dimensions of the housing 202 of the accessory discussed earlier provides suitable room to house an antenna coil 302*a* with suitable size (area) to reliability communicate with the 1 MB 10*a* at a suitable distance (for example, 12 inches or less). However, a larger antenna coil 302*a* could also be provided in the accessory 300*a* to improve communication reliability along magnetic induction link 75*a*, with the size of housing 202 adjusted accordingly.

The MDA 120 operable with accessory 300 is programmed to transmit and receive IMD data though the accessory 300's connector 204, and this can occur via the audio output signal(s) (e.g., R) and the audio input signal (MIC) in the various manners discussed earlier. Or, the MDA 120 may be programmed to attempt to communicate with the IMD with all communication means at its disposal—including those in the mobile device 100 (e.g., 125, 126) and in the accessory (301*a*, 302*a*)—and use the communication means that allows for optimal communications with the 1 MB. This may require receipt of an 1 MB acknowledgment and perhaps measurements of received signal strength. For example, the MDA 120 may first attempt to use the communication means in the mobile device 100, and if unsuccessful to then use the communication means in the accessory 300, or vice versa. In any event, in the example of FIGS. 11A-11C, once the AA 150 has verified the accessory 300*a* and executed the MDA 120, the MDA 120 establishes communications with the IMD 10*a* along magnetic induction link 75*a*.

Figure 12B:
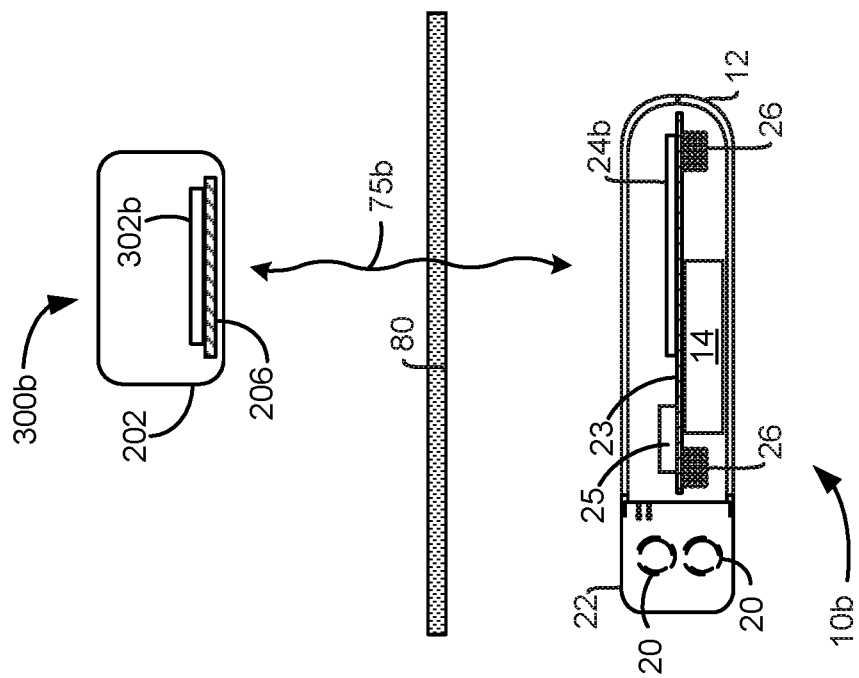
FIGS. 12A-12C show a modified accessory for a mobile device having a short-range RF antenna for communicating with an IMD in lieu of the mobile device's communication means, in accordance with an example of the invention.
Figure 12A:
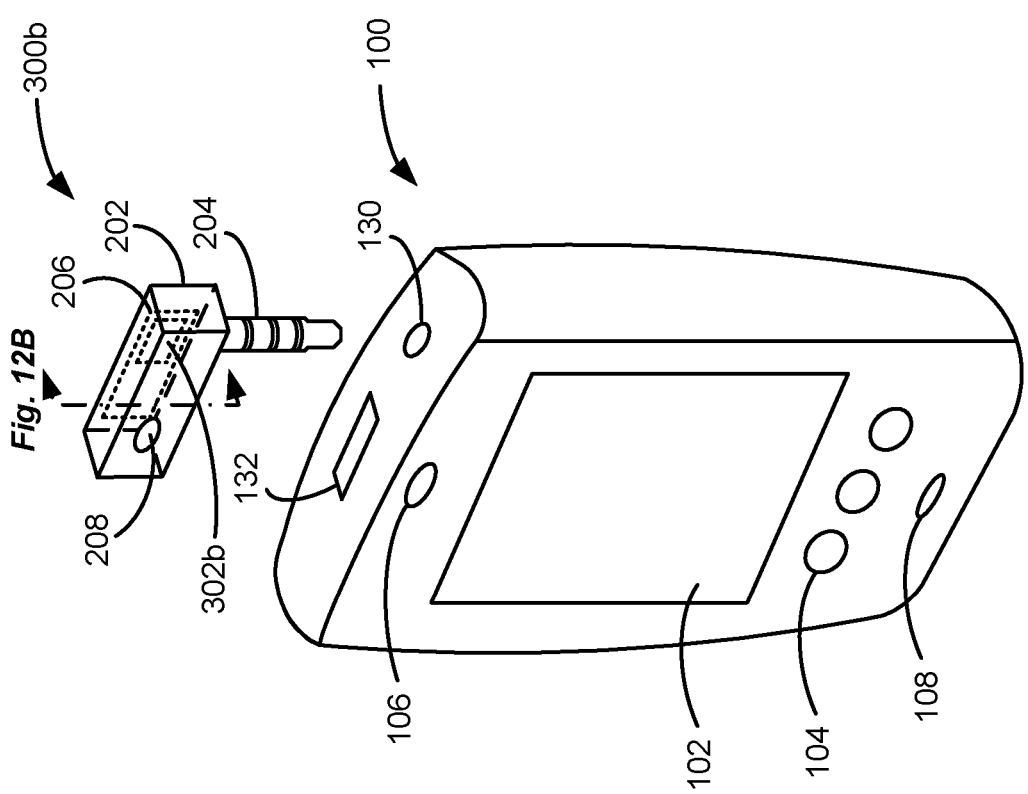
Figure 12C:
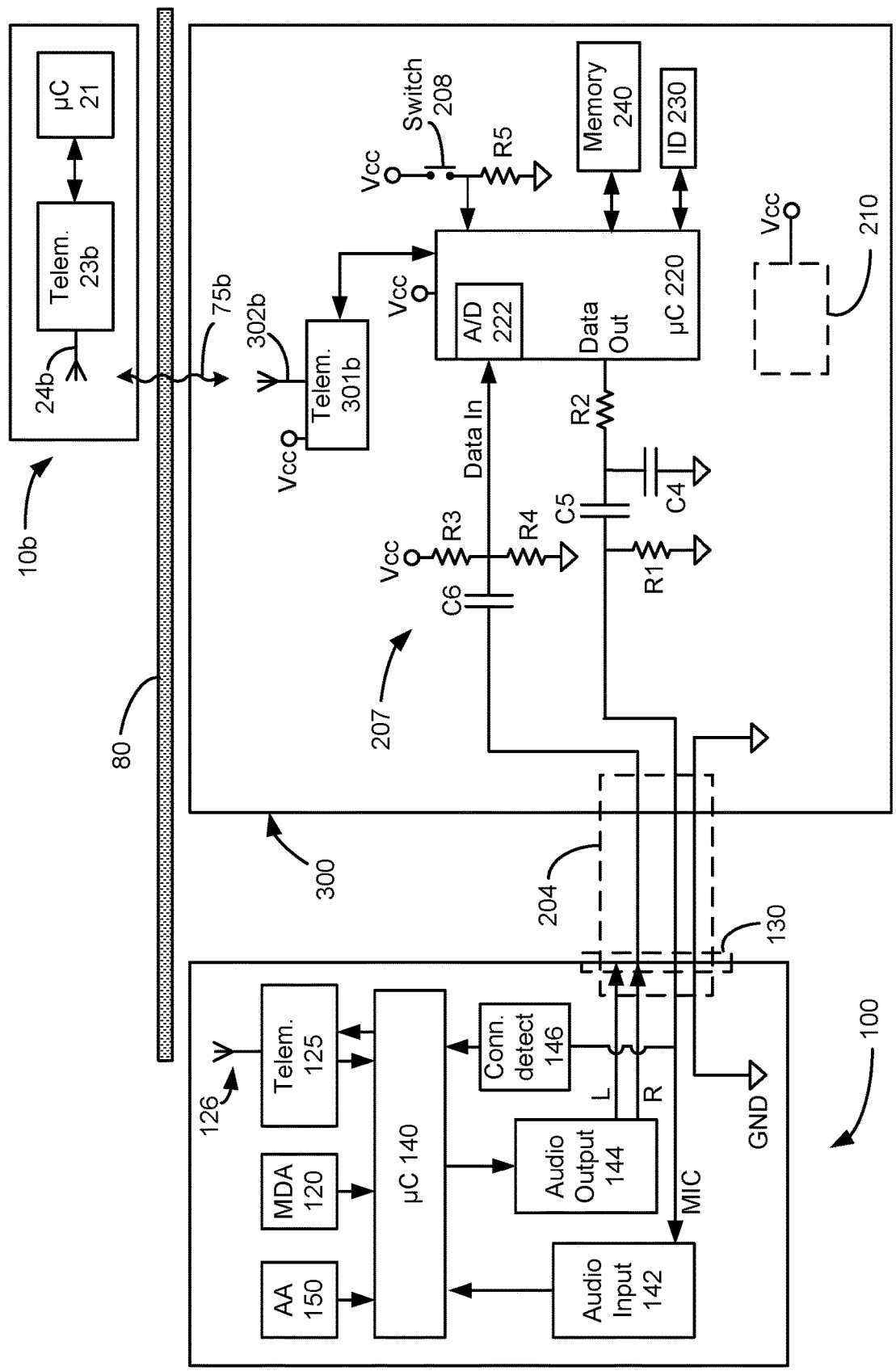

FIGS. 12A-12C show an example of an accessory 300 (300*b*) addressing the second example described above, in which IMD 10*b* has for example MICS RF communication means (e.g., FIG. 2B). To be compatible with IMD 10*b*'s communication means, the accessory 300*b* contains telemetry circuitry 301*b* operable in accordance with the MICS standard and a compliant RF antenna 302*b*. In one example, the telemetry circuitry 301*b* can comprise part number CC1101, a low-power sub-1 GHz transceiver provided by Texas Instruments, Inc. of Richardson, Tex. See http://www.ti.com/lit/ds/symlink/cc1101.pdf (data sheet). Again, such communication means are coupled to the PCB 206 in the accessory 300*b* along with the other components of FIG. 12C.

The (MICS) RF antenna 302*b* can comprise, for example, part number ANT-403-SP or ANT-403-uSP provided by Linx Technologies of Merlin Oreg., which comprise MICS-compliant antennas surface mountable to the PCB 206. See https://www.linxtechnologies.com/resources/data-guides/ant-403-sp.pdf and/ant-403-usp.pdf (data sheets). (Such antennas can also be used for RF antenna 24*b* in the IMD 10*b*). A ground plane (not shown) for antenna 302*b* can be provided as a layer in the PCB 206, or a separate ground plane can be provided in the housing 202 and coupled to the PCB 206. Again however, there are many different manners in which the RF antenna 302*b*, its ground plane, PCB 206, and its components can be arranged within the housing 202. If necessary the dimensions of the housing 202 of the accessory 300*b* can be changed to accommodate the antenna 302*b*, and to improve communication reliability along RF link 75*b*. Otherwise, the accessory 302*b*, AA 150, and MDA 120, can operate as described with respect to FIGS. 11A-C.

Although the accessories 300*a* and 300*b* are illustrated as having a single antenna 302*a* or 302*b* compatible with that used in the IMD 10*a* or 10*b*, it should be recognized that the accessory 300 could also include more than one such antenna to improve the coupling and communication reliability between the accessory 300 and the IMD. For example, although not shown, the accessories 300*a* and 300*b* could have two antennas 302*a* and 302*b* oriented along orthogonal axes within the accessory housing 202. A particular one of the orthogonal antennas could either be selected for use by the accessory 300's microcontroller 220 based on which is indicating the best coupling (e.g., signal strength) with respect to the IMD. Or, such orthogonal antennas may be driven out of phase (e.g., by 90 degrees) to produce a rotating field with better communication coverage than the use of a single antenna alone. See, e.g., U.S. Pat. No. 8,010,205 (describing antenna selection); USP 2009/0069869 (describing driving antennas out of phase); U.S. Pat. No. 8,335,569 (describing orthogonal magnetic induction antenna coils); US 2012/0004709 (describing orthogonal RF antennas). Three orthogonal antennas, or simply different numbers of antennas, may also be used with the accessories. Antenna(s) may also be placed in whole or in part outside of the accessories' housing 202.

Figure 13:
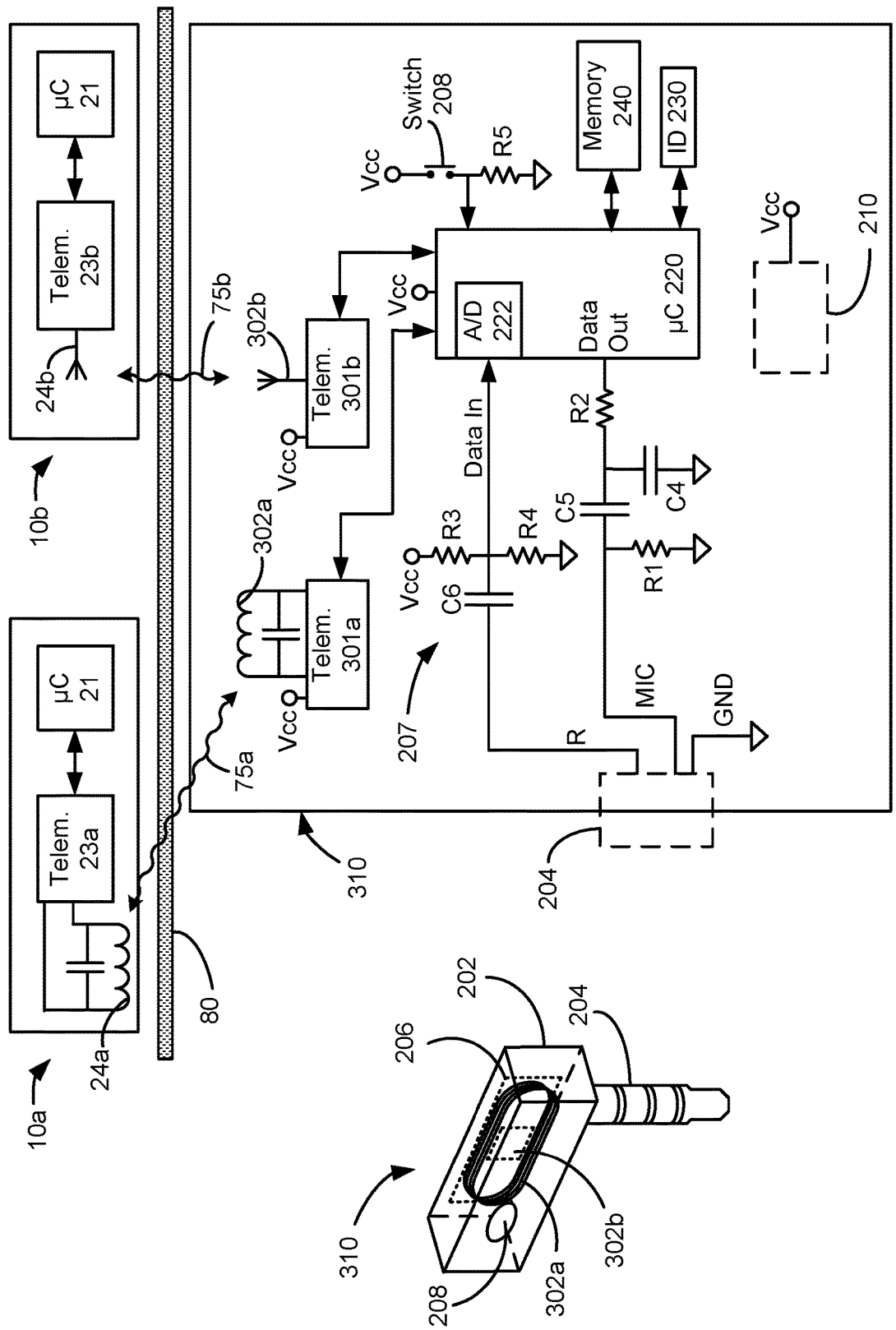
FIG. 13 shows a modified accessory for a mobile device having multiple communication means for communicating with an IMD, including a magnetic-induction antenna and a short-range RF antenna, in accordance with an example of the invention.

The accessory may also have different types of communication means to broaden the types of IMDs with which the accessory can communicate. For example, in FIG. 13, the accessory 310 has both a coil antenna 302*a* and a short-range RF antenna 302*b*, and associated compliant telemetry circuitries 301*a* (FSK) and 301*b* (e.g., MICS) in what is essentially a combination of the accessories 300*a* and 300*b* of FIGS. 11A-C and 12A-C. This further expands the utility of the accessory 310, as it can be to communicate with a wider range of implants having different types of communication means. This may be convenient to the IMD manufacturer, as it may able to manufacture a "universal" accessory 310 useable with essentially all mobile devices and with many different types of IMDs regardless of the communication means they employ. Although telemetry circuitries 301*a* and 301*b* are shown as separate in FIG. 13, they could also be integrated and coupled to both of the antennas 302*a* and 302*b*, and programmed to operate in accordance with communication schemes used on both of links 75*a* and 75*b*.

Accessory 310, the AA 150, or the MDA 120 may be programmed to enable the communication means in the accessory 310 that is appropriate for a particular patient's 1 MB. For example, the patient upon initialization and pairing of the accessory 310 to the AA 150 (see FIG. 8) may be presented with an option on the graphical user interface of the MDA 120 (not shown in FIG. 8) to select or enter the type of 1 MB the patient has, its communication means, etc. Such IMD information may then be programmed into the AA 150 or MDA 120, or stored in the accessory 310, so that the accessory 310 can subsequently enable the correct communication means (either 301a302a, or 301b/302b) in the accessory to communicate with the patient's 1 MB. If such IMD information is programmed into the AA 150 for example, it may be transmitted to the accessory 310 (per audio output R for example) at an appropriate time, such after the AA 150 validates the accessory 310 and executes the MDA 120. Of course, more than two different communications means may be provided in the "universal" accessory 310 of FIG. 13.

Note also that an accessory with one or more antennas (300a, 300b, 310) can beneficially also be used with mobile devices 100 that do not have wireless communication means, but otherwise have suitable user interfaces for IMD control. For example, some portable music players may not have wireless communication capabilities, yet will still have an audio port (normally for headphones) and a graphical user interfaces suitable to control 1 MB communications (FIG. 4B), and so can be used as an IMD external controller in conjunction with the accessory, the MDA 120, and preferably also the AA 150.

Other modifications to the various disclosed embodiments of the plug-in accessory are possible. For example, memory 240 in the accessory can contain all or part of the MDA 120 or the AA 150, which can assist in porting these applications to new mobile devices 100 as desired by the patient. For example, once the accessory is inserted in a new mobile device 100 and preferably validated, and optionally once the switch 208 is pressed, the accessory can instruct the mobile device 100 to download the portions of the MDA 120 or AA 150 stored in the accessory. Alternatively, the MDA 120 and AA 150 in the accessory may not be downloaded and permanently stored in the mobile device 100, and instead the mobile device 100 may execute the AA 150 and MDA 120 directly from the accessory, again perhaps after validation. Alternatively, only the AA 150 or the MDA 120 may be stored in the accessory. In one example, the AA 150 may be downloaded to a particular mobile device 100, thus enabling the mobile device 100 to validate the accessory and then use the MDA 120 stored in the accessory. These various alternatives again enhance physical security of the IMD control process, as control would be limited to those in possession of the accessory.

While a patient can beneficially use the accessory to execute the MDA 120 to communicate with his IMD in the various manners discussed, a mobile device 100 and AA 150 may not necessarily require the accessory to operate. For example, if a patient has misplaced his accessory, she may still be permitted to access the graphical user interface of the mobile device 100 to run the MDA 120 to communicate with the IMD as before (see FIGS. 4A and 4B), although perhaps not as quickly or securely. This being said, use of the accessory may alternatively (and preferably) be required by the mobile device 100 and the AA 150 to run or update the MDA 120 to prevent tampering in the various manners discussed above.

While use of the AA 150 in conjunction with the accessory and the MDA 120 is preferred for the benefits it provides, note that not all useful embodiments of the invention will necessarily require the AA 150 or its functionality to be used. For example, the accessory can be used to enable the MDA 120 directly with or without validation of the accessory by the AA 150, with or without preparation (e.g., unlocking, securing) of the mobile device 100 by the AA 150, etc.

One skilled in the art will understand that the disclosed applications (MDA 120, AA 150) will comprise instructions that can be stored on non-transitory machine-readable media, such as magnetic, optical, or solid-state discs, integrated circuits, tapes, etc., and which can be executed on the mobile device. Examples of likely storage devices having machine-readable media which would store the disclosed applications include the mobile device 100 (e.g., after its downloaded, on its hard drive), or an Internet or other network server, such as an implantable medical device manufacturer's server or an app store server, which a user can access to download the applications to his mobile device as noted previously. However, other storage devices could include disks, memory sticks or modules, which may be portable or which may be integrated within other computers or computer systems.

While the control circuitry in the accessory preferably comprises a microcontroller 220, other control circuits could be used as well, such as microprocessors, FPGAs, etc. An example microcontroller useable in the accessory is Part Number MSP430, manufactured by Texas Instruments, which is described in data sheets at http://www.ti.com/lsds/ti/microcontroller/16-bit_msp430/overview.page?DCMP=MCU_other&HQS=msp430, which is incorporated herein by reference. However, less complicated control circuitry could be used in the accessory depending on it construction and functionality, which as noted herein has many variations.

Although separate telemetry circuitries have been illustrated in the various devices as separate from the control circuitries (e.g., microcontrollers) which with they operate, it should be understood that such control circuitries could also include the functionality of the telemetry circuitries in whole or in part. "Control circuitry" and "telemetry circuitry" should therefore not be construed as structures that are necessarily distinct.

Although it has been assumed that the mobile device 100, the IMD, and the accessory have RF or magnetic communication abilities, the disclosed techniques can be extended to other means of wireless communications, including optical and mechanical (e.g., ultrasound) communication means. Thus, any of the communication means disclosed in these devices could be modified to operate in accordance with optical or mechanical principles, and still within the scope of the disclosed techniques.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system for wirelessly communicating with a medical device of a patient, comprising:

a first device, comprising:
 a housing, and
 controller circuitry within the housing,
 wherein the first device is configured to be communicatively coupled to a mobile device; and
a non-transitory machine-readable medium comprising instructions for a first application and a second application configured for execution on the mobile device, wherein the second application is configured to provide a graphical user interface on the mobile device,
wherein the first application is configured to:
 validate a device communicatively coupled to the mobile device as the device, and
 if the first device is validated, allow a patient to wirelessly communicate with the medical device via the graphical user interface.

2. The system of claim 1, wherein the graphical user interface is configured to allow the patient to adjust a therapy that the medical device provides to the patient.

3. The system of claim 1, further comprising the mobile device, wherein the non-transitory machine-readable medium is located in the mobile device.

4. The system of claim 3, wherein the mobile device comprises an antenna, and wherein the graphical user interface allows the patient to wirelessly communicate with the medical device using the mobile device antenna.

5. The system of claim 1, wherein the first device further comprises at least one accessory antenna.

6. The system of claim 5, wherein the graphical user interface allows the patient to wirelessly communicate with the medical device using the at least one antenna.

7. The system of claim 1, wherein the first application further comprises at least one mobile device preparation instruction to configure the mobile device to allow the patient to wirelessly communicate with the medical device via the graphical user interface.

8. The system of claim 7, wherein the at least one mobile device preparation instruction unlocks the mobile device.

9. The system of claim 7, wherein the at least one mobile device preparation instruction performs one or more of disabling a hardware module in the mobile device, reconfiguring a hardware module in the mobile device, terminating a software task in the mobile device, or temporarily suspending a software task in the mobile device.

10. The system of claim 1, wherein the controller circuitry is configured to provide validation information to the first application, and wherein the first application is configured to validate the device as the first device by assessing the validation information.

11. The system of claim 10, wherein the controller circuitry is configured to provide the validation information to the first application in response to an instruction received from the first application.

12. The system of claim 10, wherein the first device further comprises a switch on the housing activatable by the patient.

13. The system of claim 12, wherein the controller circuitry is configured to provide the validation information to the first application when the switch is activated.

14. The system of claim 10, wherein the first application is configured to detect when the first device is communicatively coupled to the mobile device, and to automatically validate the validation information in response to being communicatively coupled.

15. The system of claim 1, wherein the first device further comprises power supply circuitry configured to produce a power supply voltage for circuitry in the first device including the controller circuitry.

16. The system of claim 1, wherein the first device further comprises a connector on the housing and electrically coupled to the controller circuitry, wherein the first device is configured to be communicatively coupled to the mobile device by connecting the connector to a port on a mobile device.

17. The system of claim 1, wherein the first device further comprises a non-volatile memory.

18. The system of claim 17, wherein the second application is stored in the memory.

19. The system of claim 17, wherein the memory comprises patient therapy settings for the medical device.

20. The system of claim 1, wherein the first application and second application are either integrated into a single application or comprise separate applications.

* * * * *